(12) United States Patent
Abbosh et al.

(10) Patent No.: US 12,625,086 B2
(45) Date of Patent: May 12, 2026

(54) APPARATUS AND PROCESS FOR MEDICAL IMAGING

(71) Applicant: EMvision Medical Devices Ltd, Brisbane (AU)

(72) Inventors: Amin Abbosh, Brisbane (AU); Arman Afasri, Brisbane (AU); Ali Zamani, Brisbane (AU); Alina Bialkowski, Brisbane (AU); Guohun Zhu, Brisbane (AU); Thanh Phong Nguyen, Brisbane (AU); Lei Guo, Brisbane (AU); Yifan Wang, Brisbane (AU)

(73) Assignee: EMvision Medical Devices Ltd, Brisbane (AU)

( * ) Notice: Subject to any disclaimer, the term of this patent is extended or adjusted under 35 U.S.C. 154(b) by 830 days.

(21) Appl. No.: 17/273,247

(22) PCT Filed: Sep. 4, 2019

(86) PCT No.: PCT/AU2019/050948
§ 371 (c)(1),
(2) Date: Mar. 3, 2021

(87) PCT Pub. No.: WO2020/047599
PCT Pub. Date: Mar. 12, 2020

(65) Prior Publication Data
US 2021/0353149 A1 Nov. 18, 2021

(30) Foreign Application Priority Data

Sep. 4, 2018 (AU) ................................. 2018903284
Sep. 4, 2018 (AU) ................................. 2018903285

(51) Int. Cl.
*G01N 22/00* (2006.01)
*A61B 5/00* (2006.01)
(Continued)

(52) U.S. Cl.
CPC .......... *G01N 22/00* (2013.01); *A61B 5/0042* (2013.01); *A61B 5/0507* (2013.01);
(Continued)

(58) Field of Classification Search
None
See application file for complete search history.

(56) References Cited

U.S. PATENT DOCUMENTS

2017/0186155 A1* 6/2017 Wenzel ................... G06T 11/60
2018/0157800 A1* 6/2018 Ravishankar .......... G16H 50/50
(Continued)

FOREIGN PATENT DOCUMENTS

WO WO 2018/098387 5/2018

OTHER PUBLICATIONS

Zamani et al., "Boundary Estimation of Imaged Object in Microwave Medical Imaging Using Antenna Resonant Frequency Shift", IEEE Transactions on Antennas and Propagation, vol. 66, No. 2, pp. 927-936; Feb. 2018. (Year: 2018).*
(Continued)

*Primary Examiner* — Katherine L Fernandez
(74) *Attorney, Agent, or Firm* — KNOBBE MARTENS OLSON & BEAR, LLP

(57) ABSTRACT

A process for medical imaging, the process including:
(i) receiving scattering data representing mono-static or multi-static measurements of scattering of electromagnetic signals from tissues of a body part of a subject at a plurality of different signal frequencies, wherein electromagnetic signals are emitted from one or more antennas and the corresponding scattered signals are measured by the one or more antennas;
(ii) processing the scattering data to calculate electric field power values at each of a plurality of scattering locations of the subject's tissues within the body part and for each of the plurality of frequencies;
(Continued)

(iii) for each of the scattering locations, summing the calculated electric field power values at the scattering location over the plurality of frequencies and the plurality of antennas to generate an image of the tissues within the body part; and (iv) iteratively updating a model of the tissues within the body part based on a comparison of the model with the generated image until a termination criterion is satisfied, wherein the updated model is output as an image of the subject's tissues within the body part.

19 Claims, 24 Drawing Sheets

(51) Int. Cl.

| | | |
|---|---|---|
| *A61B 5/0507* | (2021.01) | |
| *G06N 3/084* | (2023.01) | |
| *G06V 10/764* | (2022.01) | |

(52) U.S. Cl.

CPC .......... *A61B 5/7246* (2013.01); *A61B 5/7267* (2013.01); *G06N 3/084* (2013.01); *G06V 10/764* (2022.01); *A61B 2560/0223* (2013.01); *A61B 2576/026* (2013.01)

(56) References Cited

U.S. PATENT DOCUMENTS

| | | | | |
|---|---|---|---|---|
| 2018/0299544 | A1* | 10/2018 | Shao ................... | G01S 13/0209 |
| 2019/0228857 | A1* | 7/2019 | Lin ........................ | G06N 20/00 |

OTHER PUBLICATIONS

Zhu et al., "Epileptic seizure detection in EEGs signals using a fast weighted horizontal visibility algorithm", Computer Methods and Programs in Biomedicine, vol. 115, Issue 2, pp. 64-75, Jul. 2014. (Year: 2014).*

Extended Search Report dated May 13, 2022, for European Patent Application No. 19856793.5, 12 pages.

Zhuravlev Andrey et al: Experimental comparison of multi-static and mono-static antenna arrays for subsurface radar imaging, 2015 IEEE International Conference on Microwaves, Communications, Antennas and Electronic Systems (COMCAS), IEEE, Nov. 2, 2015 (Nov. 2, 2015), pp. 1-4, XP032834851.

Zhu Guohun et al: "Epileptic seizure detection in EEGs signals using a fast weighted horizontal visibility algorithm", Computer Methods and Programs in Biomedicine, Elsevier, Amsterdam, Nl, vol. 115, No. 2, Apr. 15, 2014, pp. 64-75, XP028659702.

Chandra Rohit et al: "On the Opportunities and Challenges in Microwave Medical Sensing and Imaging", IEEE Transactions on Biomedical Engineering, IEEE, USA, vol. 62, No. 7, Jul. 1, 2015 (Jul. 1, 2015), pp. 1667-1682, XPO11584550.

Liu Xiaokun et al: "Multiple characteristics analysis of Alzheimer's electroencephalogram by power spectral density and Lempel-Ziv complexity", Cognitive Neurodynamics, Springer Netherlands, Dordrecht, vol. 10, No. 2, Nov. 12, 2015 (Nov. 12, 2015), pp. 121-133, XP035767195.

* cited by examiner

Schematic diagram of a system for brain tomography

Block diagram of an analysis component

Flow diagram of a process for brain tomography

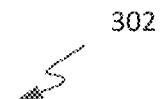
Calibration Error Model
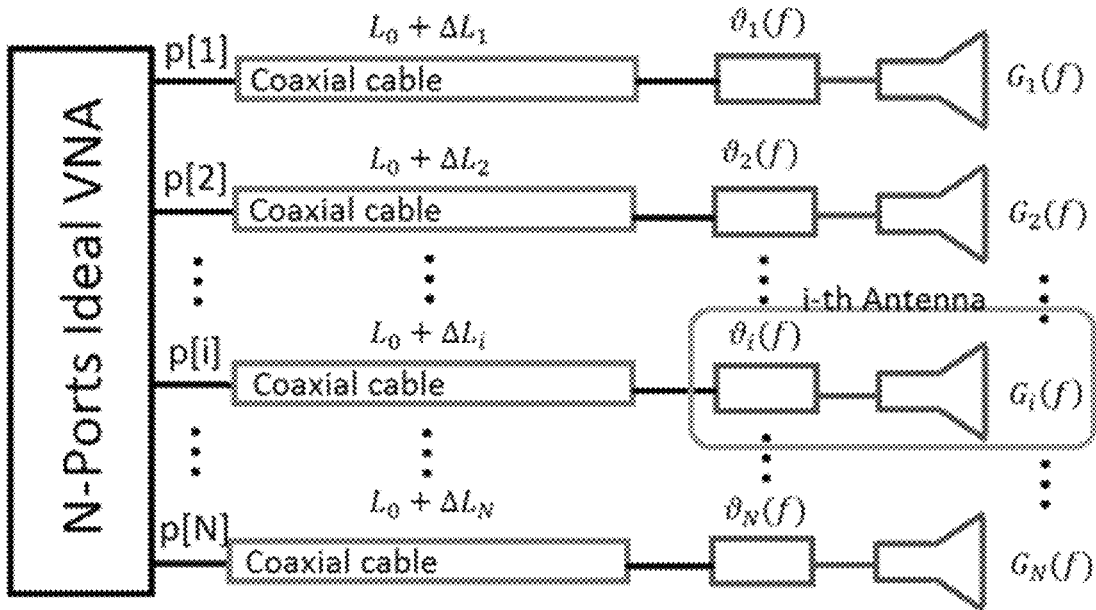
FIGURE 3a

Sensors configuration in Calibration Error Model

400
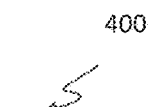
Template Generation Process_ Flowchart (400)
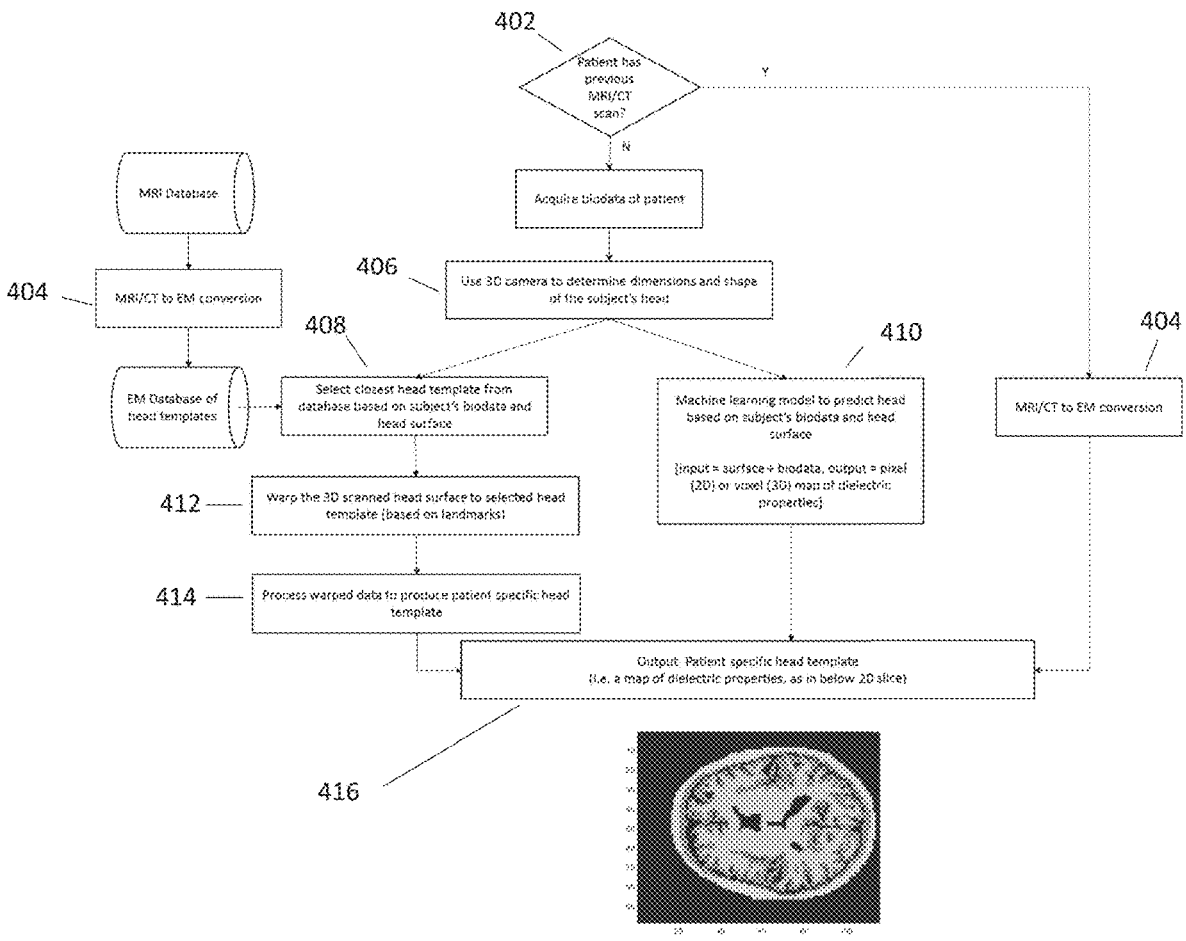
FIGURE 4a

Template Generation Process_ Visual (400)

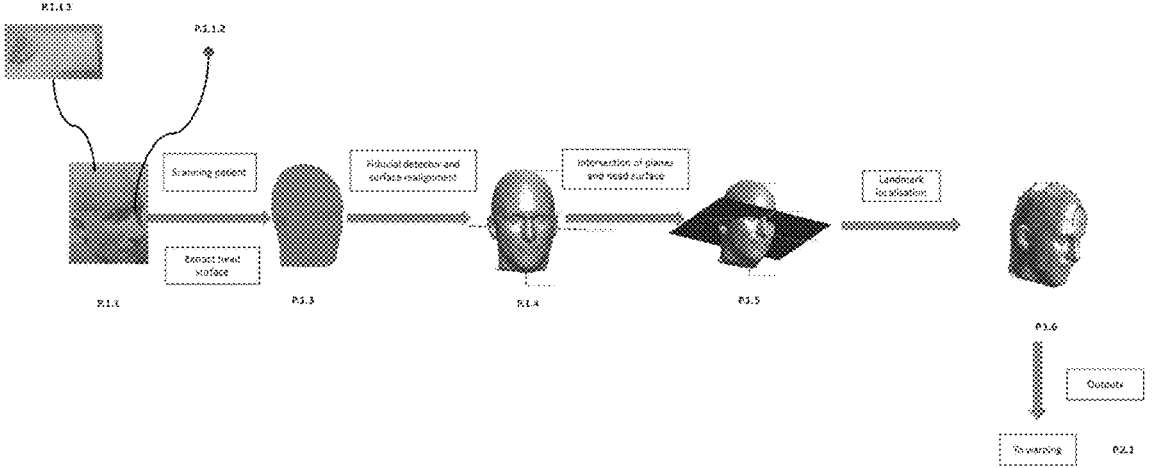

Figure descriptions:

P1.1 Input: Patient with suspected symptoms for brain injuries
     P1.1.1 A cap is placed on patient head to eliminate the effect of hair
     P1.1.2 Three circular stickers with different colours (Red, Blue, Green) are placed on fiducials (NAS, LPA and RPA, respectively).
P1.3 Patient head surface is acquired from 3D camera scan
P1.4 Fiducial localisation and realignment of head surface. Fiducials are automatically detected based on shape and colour of the stickers following by realigning scanned head to suitable coordinates.
P1.5 From fiducials, several planes are built and intersected lines between introduced planes and head surface are determined.
P1.6 Landmark distribution is determined from set of intersected lines.

FIGURE 4b

Patient specific head template 416 position within Framework in Figure 3

Flow chart for MRI to EM conversion 404
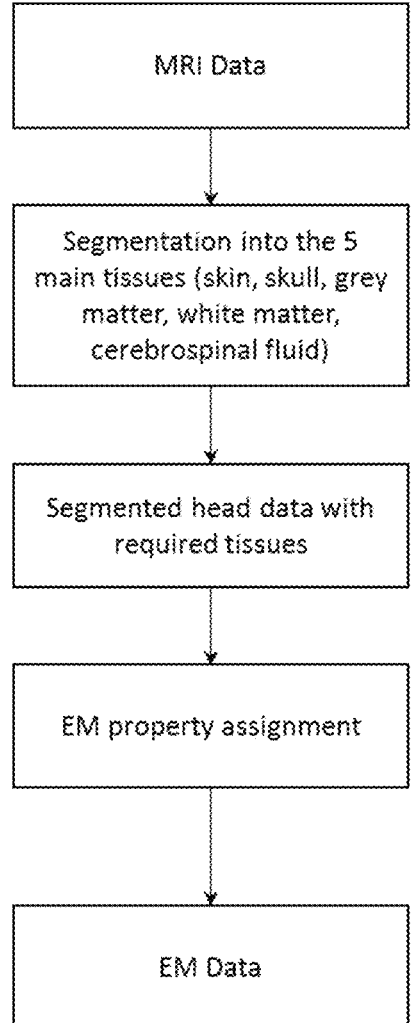
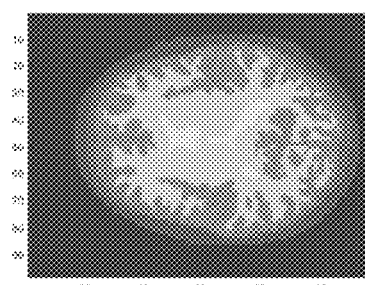
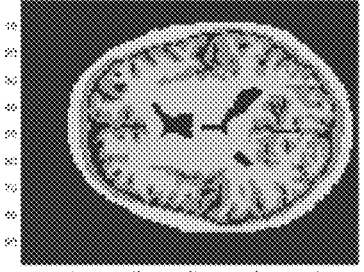
FIGURE 6

Flow diagram of an image generation (Beamography) process (308)

Functional block diagram of Beamograpghy in the analysis component

Flow diagram of a Beamography process of the image generation process

Schematic diagram illustrating the transmission of a microwave signal from a transmitting antenna into an imaging domain 312
Classification Process_ workflow of data processing and analysis steps before classification and localization
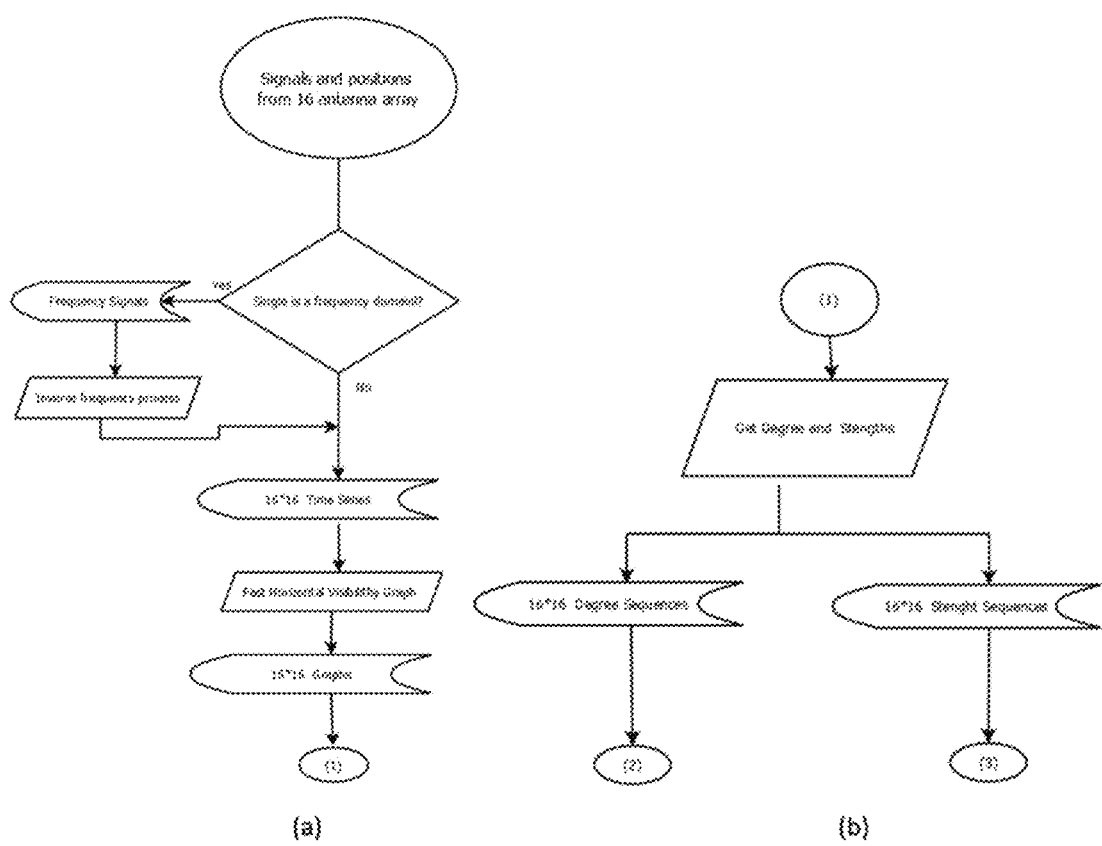
(a)                                         (b)
FIGURE 11 _workflow of pre-processing on the signals Classification Process_ describes the classification following Fig.11
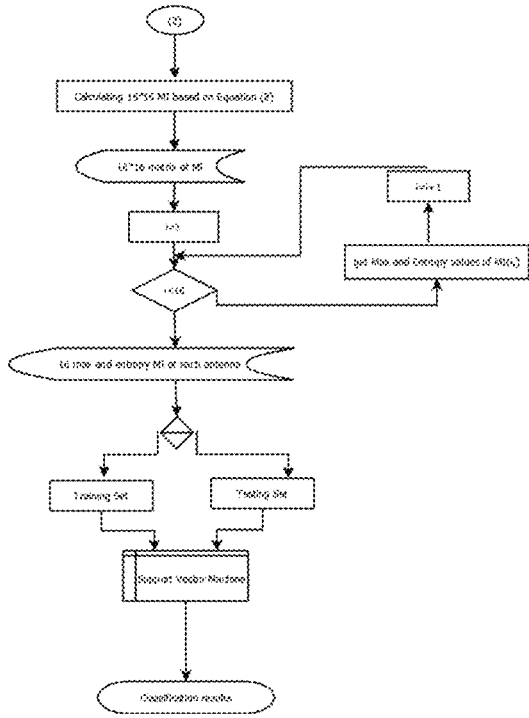
FIGURE 12_ the classification processing diagram Classification Process_ describes the localization following Fig.11
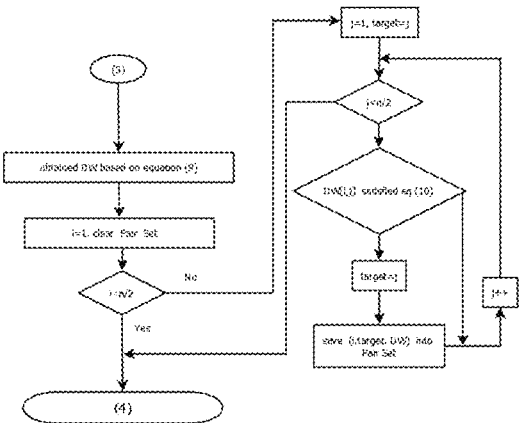
FIGURE 13_ Diagram of localization of stroke, the output will be forwarded into Fig.18

Classification Process_ Time series
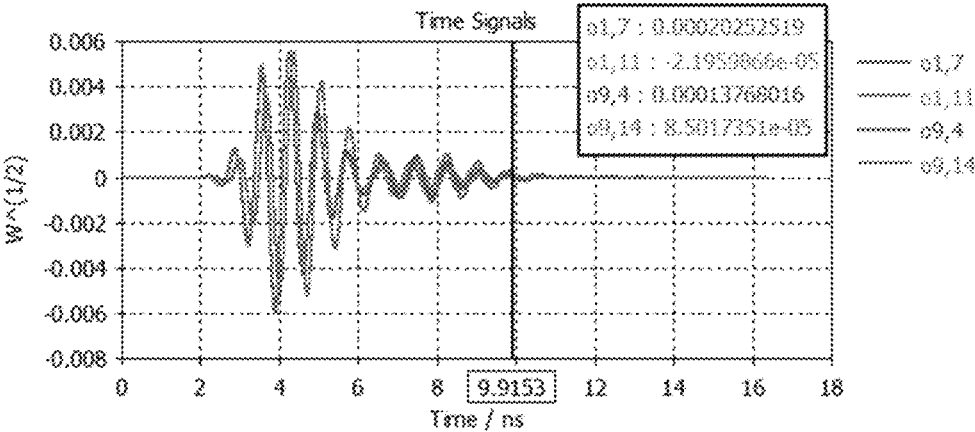
FIGURE.14 Four transmitted signals in time series Classification Process_ Frequency series
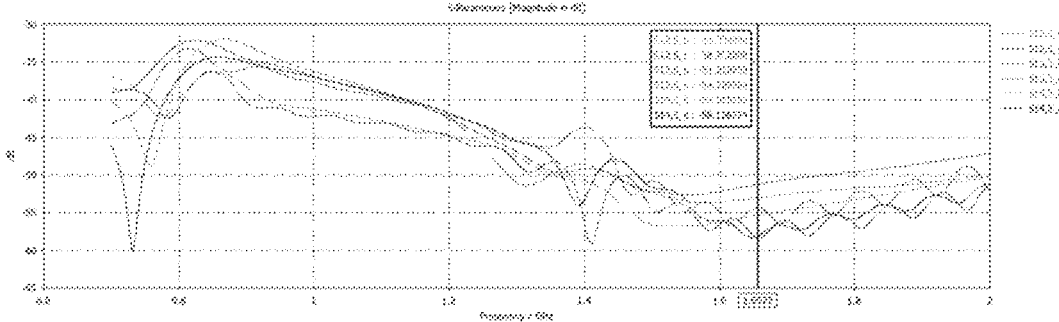
FIGURE.15 Six transmitted signals frequency domain Classification Process_ Microwave Signals and its Complex Network
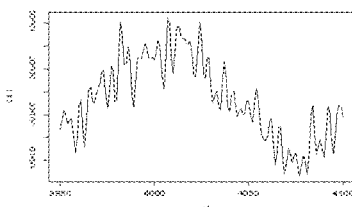 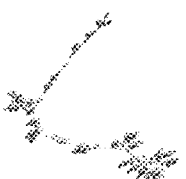
Fig.16 (a) A output reflected signals from second antenna          (b) Corresponding graph Classification Process_ Demo the weightiest pairs signals across the stroke target.

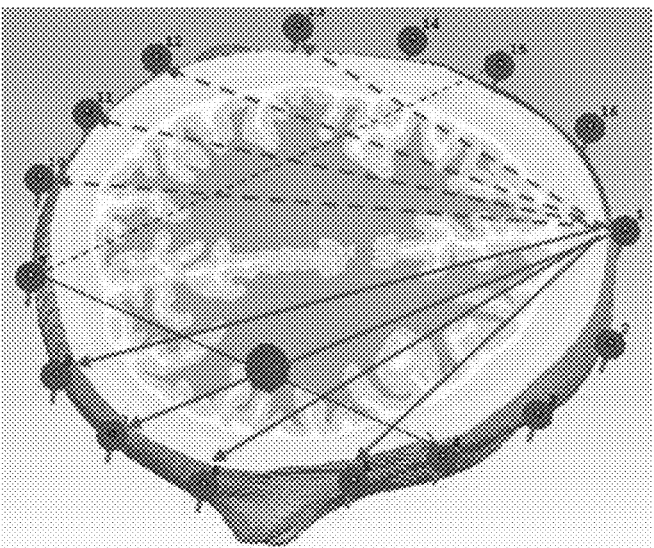

FIGURE.17_ A cross-section of the brain surrounded by a 16-element electromagnetic-imaging antenna array showing pairs of antenna signals and a stroke indicated in red. The antenna pair (1—7) will be significantly different from its symmetric pair (1—11) due to only one of the signals crossing the stroke. However, the 1—13 and the 1—5 antenna pairs should have similar received signals Classification Process_ flowchart of localization
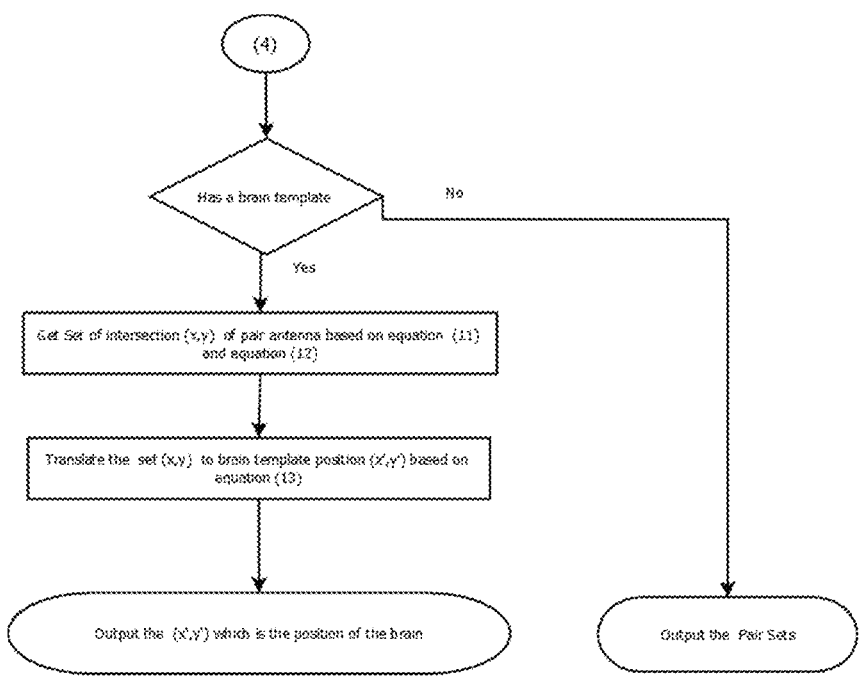
FIGURE.18_ output of localization Classification Process_ Localization results_ A bleeding model from Duke Stroke brain model.
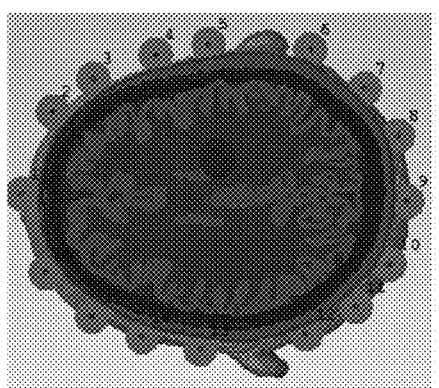 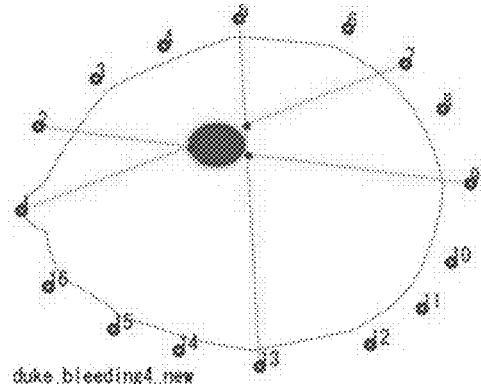
FIGURE.19_ the pairs (1—7) and pairs (2—9) can be used for detected the localization of stroke place 310
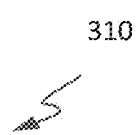
Image Fusion Process 310
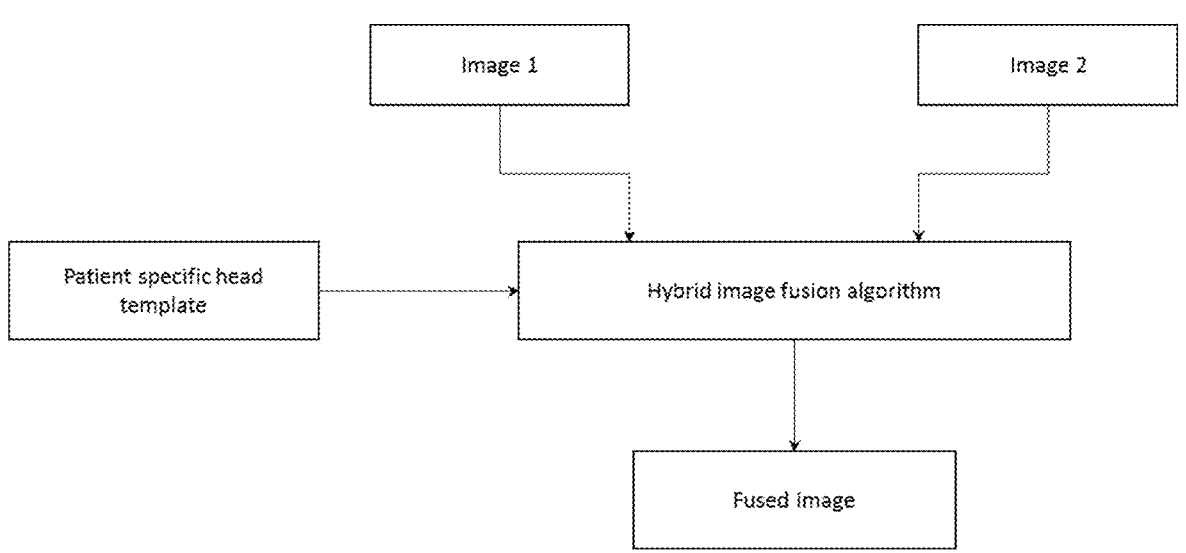
FIGURE 20

APPARATUS AND PROCESS FOR MEDICAL IMAGING

This application is a U.S. national phase application under 35 U.S.C. § 371 of international patent application No. PCT/AU2019/050948, filed on Sep. 4, 2019, and entitled "APPARATUS AND PROCESS FOR MEDICAL IMAGING," which claims priority to Australian patent application No. 2018903284, filed on Sep. 4, 2018, and to Australian patent application No. 2018903285, filed on Sep. 4, 2018, the entire contents of each of which are incorporated herein by reference.

TECHNICAL FIELD

The present invention relates to the field of medical imaging, in particular using signal processing and electromagnetic computational techniques to detect the presence and location of abnormalities inside tissues and to classify such abnormalities.

BACKGROUND

Medical imaging technologies such as ultrasound, computed tomography (CT), magnetic resonance imaging (MRI) and nuclear medicine imaging are extremely powerful techniques for imaging internal features of the human body, but suffer from a number of disadvantages that limit their applicability. For example, these technologies require expensive equipment, and are therefore not generally available at rural or remote health centres. Indeed, according to the World Health Organization (WHO), more than half of the world's population does not have access to diagnostic imaging. Furthermore, there is a general need for low-cost and safe imaging systems for the detection and continuous monitoring of a variety of diseases. Due to the need to limit exposure to ionising radiation such as X-rays, most currently available medical imaging systems cannot be used for frequent monitoring. Additionally, the bulky and static structures and high costs of MRI and other large medical imaging systems often preclude them for monitoring diseases that require activity monitoring on a regular and short-term basis, and is impractical for them to be used by paramedics for on the spot imaging and assessment purposes.

Furthermore, conventional medical imaging tools are generally not suitable for urgent onsite diagnosis. For example, brain strokes are one of the main causes of disability and death worldwide. According to the Australian Stroke Foundation Organization, in 2017 55,831 Australians suffered a life-threatening stroke every nine minutes, and without taking an action this number will increase to one stroke every four minutes by 2050. Similarly, in case of brain injuries, rapid diagnosis is often essential to save the patient. Severe brain injuries include traumatic and acquired brain injuries, which are respectively caused by external forces (such as a fall or accident) or internal incidences (such as a stroke or tumor). It is well known that a patient with a brain injury requires immediate medical attention. From the onset of the brain injury, millions of brain cells die every second, causing permanent damage and in some cases death. Thus, a rapid and portable diagnosis system is required for rapid on the spot diagnosis of such injuries.

Electromagnetic imaging is an attractive technique for medical applications, and has the potential to create a visual representation of the interior of the human body in a cost-effective and safe manner. From an electromagnetic engineering perspective, the human body is an electromagnetically heterogeneous medium characterized by features and tissues with different dielectric properties. Moreover, an injured tissue has different values of the dielectric properties permittivity and conductivity compared to healthy tissues. When an injured tissue with a high permittivity value compared to its neighbouring healthy tissue is exposed to an electromagnetic wave at a microwave frequency, a high portion of the wave is reflected back towards the radiation source. A microwave medical imaging system can be utilized to transmit electromagnetic waves into an object to be imaged, such as the human head. Microwave signals reflected by damaged tissues within the head (e.g., in particular at bleeding or clot sites within the brain) due to changes in electromagnetic properties are received and measured by the system, and data representing the measured signals can be processed to estimate the location and/or dielectric properties of the abnormality, and to generate two or three-dimensional images of the head showing the damaged tissues.

The data processing step plays a critical role in an electromagnetic imaging system. Various imaging techniques have been employed to detect medical targets from measurements of scattered electromagnetic signals. Those techniques try to estimate the dielectric properties of the tissues by solving nonlinear equations (tomography), which do not have a unique solution, and that solution may not depend continuously on the input data, or to find the location of target using time-domain radar-based techniques. Due to the time-consuming nature of tomography-based techniques, they are almost exclusively applicable to single frequency or narrow-band multi-frequency signals, and are therefore not suitable for use in medical emergency situations such as brain injury detection, where a rapid diagnosis is required. Alternatively, in radar-based imaging, a scattering profile of the imaging domain is mapped onto a two- or three-dimensional image. This method is more applicable when using ultra-wide frequency bands for fine resolution because the required data processing is simpler and faster than tomography. However, current radar imaging methods, such as confocal, space-time beamforming MIST, and adaptive beamforming imaging methods utilize processing techniques based on delay-and-sum (DAS), which are susceptible to outer layer reflections and internal layer refractions that can result in false detection. In addition, the variation of signal penetration through the tissues at different frequencies limits the effectiveness of those delay calculations, and consequently the accuracy of the resulting images. In view of these difficulties, a rapid imaging process that does not suffer from the non-unique and computationally expensive solutions of tomographic techniques or inaccurate processing due to multi-reflection and refractions of the heterogeneous multilayer structure of the human body is required.

It is desired, therefore, to overcome or alleviate one or more difficulties of the prior art, or to at least provide a useful alternative.

SUMMARY

In accordance with some embodiments of the present invention, there is provided a process for medical imaging, the process including:

(i) receiving scattering data representing mono-static or multi-static measurements of scattering of electromagnetic signals from tissues of a body part of a subject at a plurality of different signal frequencies, wherein electromagnetic signals are emitted from one or more antennas and the corresponding scattered signals are measured by the one or more antennas;

(ii) processing the scattering data to calculate electric field power values at each of a plurality of scattering locations of the subject's tissues within the body part and for each of the plurality of frequencies;

(iii) for each of the scattering locations, summing the calculated electric field power values at the scattering location over the plurality of frequencies and the plurality of antennas to generate an image of the tissues within the body part; and (iv) iteratively updating a model of the tissues within the body part based on a comparison of the model with the generated image until a termination criterion is satisfied, wherein the updated model is output as an image of the subject's tissues within the body part.

In some embodiments, the measurements are multi-static measurements wherein electromagnetic signals are selectively emitted from each of a plurality of antennas disposed about the body part and the corresponding scattered signals are measured by each of the plurality of antennas.

The body part may be a head, and the tissues include brain tissues of the subject.

In some embodiments, the process includes:

(v) processing biodata of the subject using machine learning to select, from a library of templates, a base template as being the best match for the subject, wherein the templates represent respective models of tissues of the body part of respective subjects, and the biodata of the subject represents at least age, gender, weight, and ethnicity of the subject;

(vi) processing the selected base template and measurements of outer dimensions and/or shape of the subject's body part to generate template data representing the model of the subject's body part tissues by geometrically transforming spatial coordinates of the selected template to match the measurements of the subject's body part.

In some embodiments, the step of processing the scattering data includes the steps of:

(vii) normalising and removing clutter from the scattering data; and (viii) processing the normalised and clutter removed scattering data to calculate the electric field power values.

In some embodiments, removing clutter from the scattering data includes determining an average value of the measured electromagnetic signals and subtracting the average value from each signal measurement at each frequency to remove strong reflections and clutter from the scattering data.

In some embodiments, the process includes calibrating the scattering data by dividing the measured scattering parameters for the body part by measured scattering parameters of the imaging domain in the absence of the body part and with the imaging domain filled by a material with dielectric properties of a matching medium or an average body part phantom.

In some embodiments, the process includes classifying abnormal tissues within the body part as haemorrhagic or ischemic, by converting frequency domain signals to time-domain signals and mapping the time-domain signals to a corresponding graph, determining node degree and degree sequence properties of the graph, calculating graph degree mutual information to assess similarity of graphs, and training a classifier with a training set of graph degree mutual information features and their corresponding class labels and applying the classifier to the graphs calculated for the subject's tissues within the body part.

In some embodiments, the process includes comparing signals for corresponding pairs of opposed antennas to identify significant differences between the signals for different hemispheres of the subject's brain, these being indicative of an abnormality in one of the hemispheres.

In accordance with some embodiments of the present invention, there is provided a computer-readable storage medium having stored thereon processor-executable instructions that, when executed by at least one processor of a medical imaging system, cause the at least one processor to execute any one of the above processes.

In accordance with some embodiments of the present invention, there is provided an apparatus for medical imaging, including components configured to execute any one of the above processes.

In accordance with some embodiments of the present invention, there is provided an apparatus for medical imaging, including:

(i) an input to receive scattering data representing mono-static or multi-static measurements of scattering of electromagnetic signals from tissues of a body part of a subject at a plurality of different signal frequencies, wherein electromagnetic signals are emitted from one or more antennas and the corresponding scattered signals are measured by the one or more antennas; and (ii) an image generation component configured to:

process the scattering data to calculate electric field power values at each of a plurality of scattering locations of the subject's tissues within the body part and for each of the plurality of frequencies;

for each of the scattering locations, sum the calculated electric field power values at the scattering location over the plurality of frequencies and the plurality of antennas to generate an image of the tissues within the body part; and iteratively update a model of the tissues within the body part based on a comparison of the model with the generated image until a termination criterion is satisfied, wherein the updated model is output as an image of the subject's tissues within the body part.

In some embodiments, the measurements are multi-static measurements wherein electromagnetic signals are selectively emitted from each of a plurality of antennas disposed about the body part and the corresponding scattered signals are measured by each of the plurality of antennas.

In some embodiments, the body part is a head and the tissues include brain tissues of the subject.

In some embodiments, the apparatus includes a template generator to:

process biodata of the subject using machine learning to select, from a library of templates, a base template as being the best match for the subject, wherein the templates represent respective models of tissues of the body part of respective subjects, and the biodata of the subject represents at least age, gender, weight, and ethnicity of the subject; and process the selected base template and measurements of outer dimensions and/or shape of the subject's body part to generate template data representing the model of the subject's body part tissues by geometrically transforming spatial coordinates of the selected template to match the measurements of the subject's body part.

Also described herein is a process for imaging tissues of a body part of a subject, the process including:

(i) processing biodata of the subject using machine learning to select, from a library of templates, a template as being the best match for the subject, wherein the templates represent respective models of tissues of the body part of respective subjects, and the biodata of the subject represents at least age, gender, weight, and ethnicity of the subject;

(ii) processing the selected template and measurements of outer dimensions and/or shape of the subject's body part to generate template data representing a model of the subject's body part tissues by geometrically transforming spatial coordinates of the selected template to match the measurements of the subject's body part;

(iii) receiving scattering data representing multi-static measurements of microwave scattering from body part tissues of the subject at a plurality of different signal frequencies;

(iv) normalising and removing clutter from the scattering data;

(v) processing the normalised and clutter removed scattering data to calculate electric field power densities at each of a plurality of scattering locations of the subject's body part tissues and for each of the plurality of frequencies;

(vi) for each of the scattering locations, summing the calculated electric field power densities at the scattering location over the plurality of frequencies to generate an image of the subject's body part tissues; and (vii) iteratively updating the model of the tissues of the subject's body part based on a comparison of the model with the generated image until a termination criterion is satisfied, wherein the updated model is output as an image of at least the subject's body part tissues.

In some embodiments, the body part of the subject is the subject's head.

Also described herein is a process for imaging brain tissues of a subject, the process including:

(i) processing biodata of the subject using machine learning to select, from a library of templates, a template as being the best match for the subject, wherein the templates represent respective models of head tissues of respective subjects, and the biodata of the subject represents at least age, gender, weight, and ethnicity of the subject;

(ii) processing the selected template and measurements of outer dimensions and/or shape of the subject's head to generate template data representing a model of the subject's head tissues by geometrically transforming spatial coordinates of the selected template to match the measurements of the subject's head;

(iii) receiving scattering data representing multi-static measurements of microwave scattering from brain tissues of the subject at a plurality of different signal frequencies;

(iv) normalising and removing clutter from the scattering data;

(v) processing the normalised and clutter removed scattering data to calculate electric field power densities at each of a plurality of scattering locations of the subject's brain tissues and for each of the plurality of frequencies;

(vi) for each of the scattering locations, summing the calculated electric field power densities at the scattering location over the plurality of frequencies to generate an image of the subject's brain tissues; and (vii) iteratively updating the model of the tissues of the subject's head based on a comparison of the model with the generated image until a termination criterion is satisfied, wherein the updated model is output as an image of at least the subject's brain tissues.

Also described herein is a process for medical imaging of a subject, the process including:

(i) receiving scattering data representing multi-static measurements of scattering of electromagnetic signals from tissues of the subject at a plurality of different signal frequencies;

(ii) processing the scattering data to calculate electric field power densities at each of a plurality of scattering locations of the subject's tissues and for each of the plurality of frequencies;

(iii) for each of the scattering locations, summing the calculated electric field power densities at the scattering location over the plurality of frequencies to generate an image of the subject's tissues; and (iv) iteratively updating a model of the subject's tissues based on a comparison of the model with the generated image until a termination criterion is satisfied, wherein the updated model is output as an image of the subject's tissues.

In some embodiments, the tissues include brain tissues of the subject.

BRIEF DESCRIPTION OF THE DRAWINGS

Some embodiments of the present invention are hereinafter described, by way of example only, with reference to the accompanying drawings, wherein:

FIG. 3a is a block diagram of a calibration model of a calibration process of the imaging process of FIG. 3;

FIGS. 4a & b are flow diagrams of a template generation process of the imaging process of FIG. 3;

FIG. 6 is a flow diagram of an MRI to EM conversion process of the imaging process;

FIGS. 11 to 19 illustrate different portions or sub-processes of a classification process of the imaging process, as follows:

FIG. 11 is a flow diagram of data processing and analysis steps of the classification process before classification and localization;

FIG. 12 is a flow diagram of the classification following the steps of FIG. 11;

FIG. 13 is a flow diagram of the localization steps following FIG. 11;

FIG. 14 is a graph of Time series signals generated by the system;

FIG. 15 is a graph of Frequency domain signals generated by the system;

FIG. 16A and b are respectively a graph of Microwave Signals and its Complex Network graph;

FIG. 17 is a schematic diagram illustrating that the differential weightiest pairs of signals cross a stroke target;

FIG. 18 is a flow diagram of localization steps of the classification process;

FIG. 19 includes images of a bleeding model from the Duke Stroke brain model;

FIG. 20 illustrates an image fusion process of the imaging process; and

DETAILED DESCRIPTION

The electromagnetic imaging system and process described herein are able to rapidly generate images of internal structures within an object in a safe manner. Although the described system and process have been developed for the primary purpose of detecting and characterising internal injuries and/or diseases in human subjects (particularly within the human brain), and are described herein within that context, it should be understood that many aspects of the system and process can be applied to other parts of the human body, to other living creatures, and even to non-living or inanimate objects.

Figure 1:
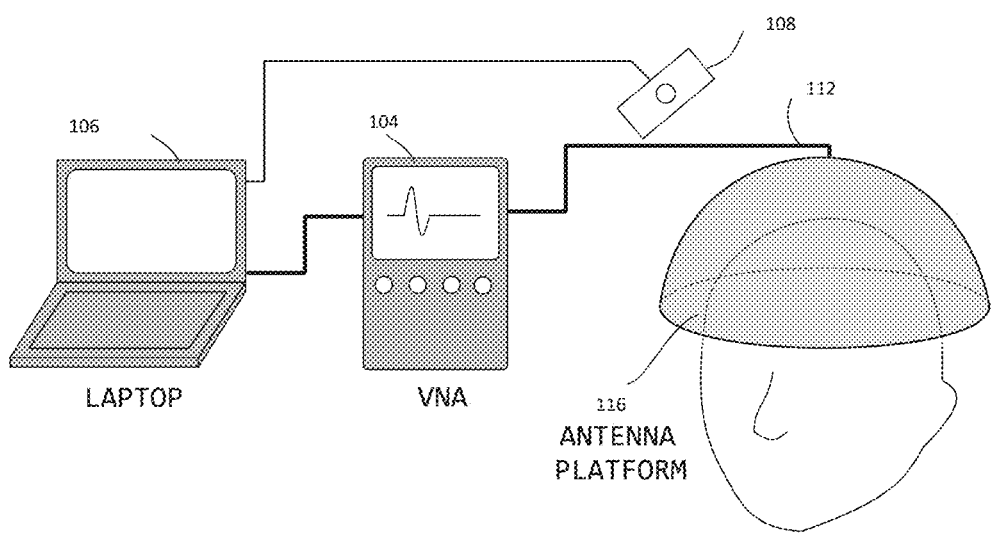
FIG. 1 is a schematic diagram of an electromagnetic medical imaging system in accordance with an embodiment of the present invention.

As shown in FIG. 1, a system for medical imaging, and in particular for detecting brain injuries, includes an antenna assembly or platform 102 which includes an antenna array, a vector network analyser (VNA) or transceiver 104, and an analysis component 106. In the described embodiments, the antenna assembly or platform 102 is placed on the head of a human subject whose brain is to be imaged, as shown in FIG. 1. The antenna platform 102 includes an array of antennas disposed about the subject so that each antenna of the array can be selectively energised to radiate electromagnetic waves or signals of microwave frequency into and through the subject's head to be scattered and the corresponding scattered signals detected by all of the antennas of the array, including the antenna that transmitted the corresponding signal. For convenience of reference, the overall process of sequentially causing each antenna of the array to transmit a corresponding microwave signal and using all of the antennas to receive the corresponding scattered signals is referred to as 'a scan'.

As will be apparent to those skilled in the art, the vector network analyser (VNA) 104 energises the antennas as described above, and records the corresponding signals from the antennas as data (referred to herein as 'scattering' data) representing the amplitudes and phases of the scattered microwaves in a form that is known in the art as "scattering parameters" or "S-parameters". The VNA 104 sends this data to the analysis component 106 for processing to generate images of internal features of the imaged object (e.g., brain clots, bleeding sites, and other features) and to classify those features (e.g., as brain clots or bleeding sites). In the described embodiments, a VNA which has a large dynamic range of more than 100 dB and a noise floor below −100 dBm, it is used to activate the antennas to transmit electromagnetic signals across the frequency band of 0.5 to 4 GHz and to receive the scattered signals from those antennas.

Figure 2:
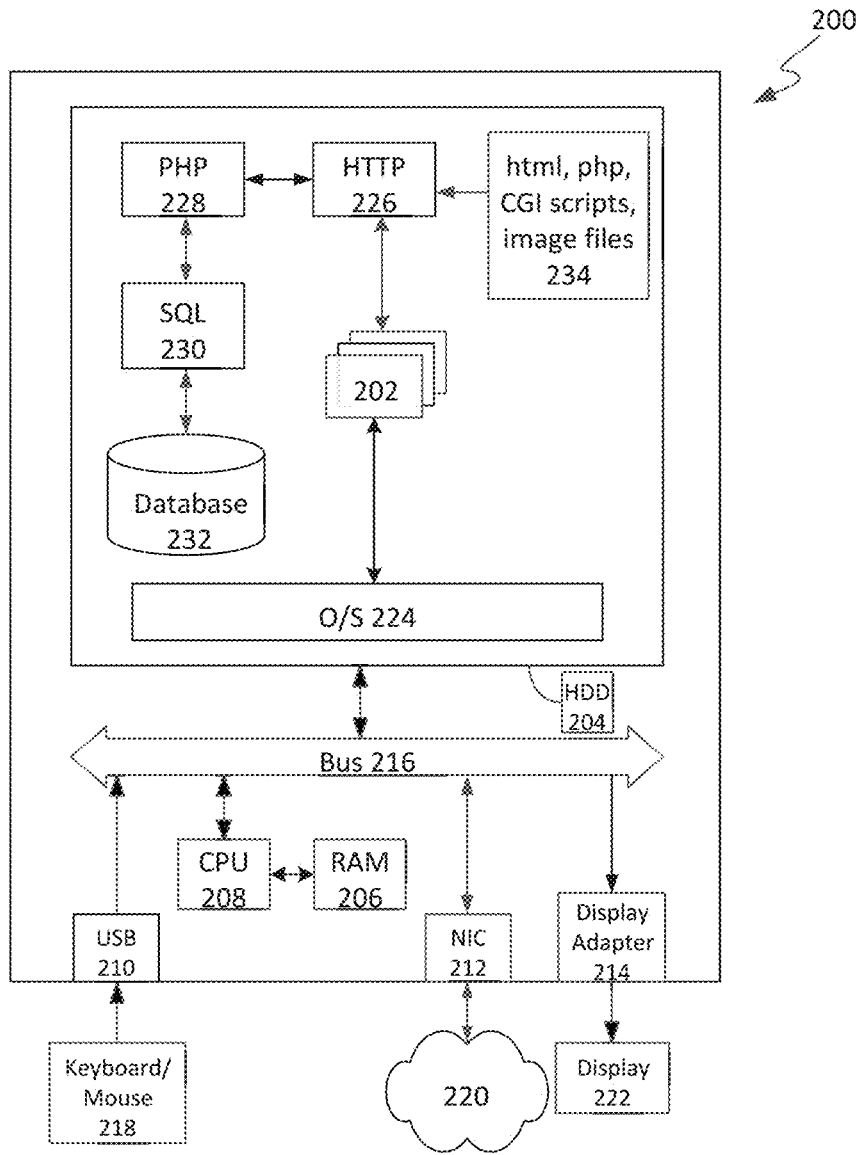
FIG. 2 is a block diagram of an analysis component of the system of FIG. 1.

Although the analysis component 106 of the described embodiments is (as shown in FIG. 1) in the form of a computer, this need not be the case in other embodiments. As shown in FIG. 2, the analysis component 106 is a 64-bit Intel Architecture computer system, as shown in FIG. 2, and the processes executed by the analysis component 106 are implemented as programming instructions of one or more software modules 202 stored on non-volatile (e.g., hard disk or solid-state drive) storage 204 associated with the computer system. However, it will be apparent that at least parts of these processes could alternatively be implemented as one or more dedicated hardware components, such as application-specific integrated circuits (ASICs) and/or configuration data for one or more field programmable gate arrays (FPGAs), for example.

The analysis component 106 includes standard computer components, including random access memory (RAM) 206, at least one processor 208, and external interfaces 210, 212, 214, all interconnected by a bus 216. The external interfaces include universal serial bus (USB) interfaces 210, at least one of which is connected to a keyboard 218 and a pointing device such as a mouse 219, a network interface connector (NIC) 212 which connects the analysis component 106 to a communications network such as the Internet 220, and a display adapter 214, which is connected to a display device such as an LCD panel display 222.

The analysis component 106 also includes a number of standard software modules 226 to 230, including an operating system 224 such as Linux or Microsoft Windows. In the described embodiment, the analysis component 106 also includes web server software 226 such as Apache, available at http://www.apache.org, scripting language support 228 such as PHP, available at http://www.php.net, or Microsoft ASP, and structured query language (SQL) support 230 such as MySQL, available from http://www.mysql.com, which allows data to be stored in and retrieved from an SQL database 232.

Together, the web server 226, scripting language module 228, and SQL module 230 provide the analysis component 106 with the general ability to allow users of the Internet 220 with standard computing devices equipped with standard web browser software to access the analysis component 106 and in particular to provide data to and receive data from the database 232.

However, it will be understood by those skilled in the art that the specific functionality provided by the analysis component 106 to such users is provided by scripts accessible by the web server 226, including the one or more software modules 202 implementing the processes, and also any other supporting scripts and data 234, including markup language (e.g., HTML, XML) scripts, PHP (or ASP), and/or CGI scripts, image files, style sheets, and the like.

Figure 3:
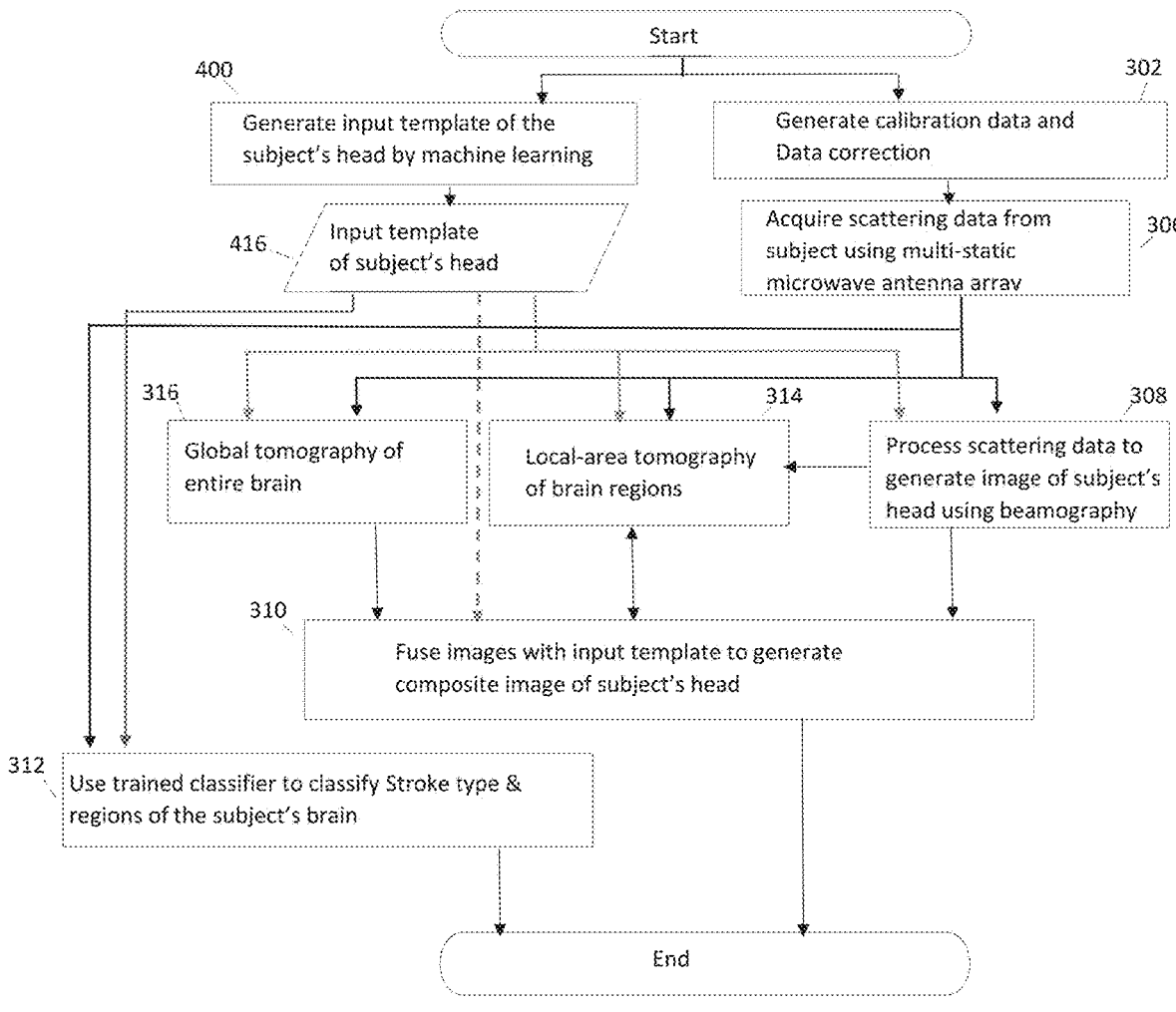
FIG. 3 is a flow diagram of an electromagnetic medical imaging process in accordance with an embodiment of the present invention.

The system described herein executes a medical imaging process, also referred to herein as a process for brain imaging, as shown in FIG. 3. This process begins by generating calibration data for the antenna platform 116 at step 302. The image reconstruction and classification processes executed by the system rely on high-fidelity data collected from the antennas. However, in any real scenario, the system uses radio frequency (RF) cables with different lengths and bending profiles, connected with different adapters and antenna baluns. Furthermore, the antennas themselves are always slightly different due to: 1) manufacturing variations/errors, and 2) unstable dielectric properties of the medium in which the antennas are embedded. Such uncertain variations among different RF channels (including cables, adapters, and antennas) within the system introduce signal differences in both amplitude and phase, and ultimately producing measurement errors that degrade the detection, resolution and reliability of imaging reconstruction/classification.

To mitigate the effects of these variations and distortions, the system includes a frequency-domain calibration component and a corresponding data calibration process to remove or at least reduce the measurement errors. In practice, the calibration process is ideally executed immediately prior to each scan of a subject, but can alternatively be executed less often; for example, only at the start of each day.

Assuming the VNA 104 has been well calibrated on all of its N ports, the calibration model for the system employs a particular transmission-line error model and antenna uncertainty matrix, as shown in FIG. 3a. The transmission line error model on the left side represents the coaxial cables and cascaded adapters connected from each VNA port to the corresponding antenna element. Since the coaxial lines (and adapters) are of good transmission quality with negligible insertion loss, the biggest variance among those cables is mainly produced from their bending profile and effective physical length errors ($\Delta L_i$). Suppose the desired length for all cables is $L_0$, the effective length of the cable (including the adapter) in channel-i can be expressed as $L_0 + \Delta L_i << L_0$). At the same time, consider that the antenna element and its balun employed in the same channel has a level of phase-delay and gain uncertainties, as represented by a frequency-dependent phase shifter $\vartheta_i(f)$ cascaded with a directional point source with a frequency-dependent gain $G_i(f)$. Because the directional point source in this model is located at the same position with the antenna phase centre, it doesn't contribute any phase shift by itself.

In this model, each channel has three error parameters, the first error arises from the coaxial cable and adapter ($\Delta L$), and the other two errors [G(f), $\vartheta$(f)] arise from the antenna element and its balun. The following calibration process determines those error parameters for the purpose of correcting the measured S-parameters before implementing the image reconstruction/classification processes described below.

Step #1: For each RF channel, place a reflecting object directly in contact with the antenna element to invalidate its radiation aperture and generate short-circuit reflections. (For an aperture-based antenna, such as an open-ended waveguide, the short circuit configuration can be implemented by a perfect-E boundary condition that overlaps with the assigned radiation aperture; for a resonance-based antenna, such as a dipole or bowtie, a short circuit configuration can be generated by bonding a via that is connected immediate to its feeding section so that the antenna does not resonate).

Then, record the $S_{ii}$ data {$S_{11}$, $S_{22}$, . . . , $S_{NN}$} from the N-port VNA 104. In this case, $$|s_{ii}(f)| \cong 1$$

$$\angle S_{ii}(f) = \pi + 2\beta(L_0 + \Delta L_i) + 2\vartheta_i(f) = \pi + 4\pi f L_0 / c + 2(2\pi f \Delta L_i / c + \vartheta_i(f))$$

$$\text{Let } P_i(f) = (2\pi f \Delta L_i / c + \vartheta_i(f)),$$

$$\text{we have } P_i(f) = \frac{1}{2}(\angle S_{ii}(f) - \pi) - \frac{2\pi f L_0}{c}$$

Figure 3B:
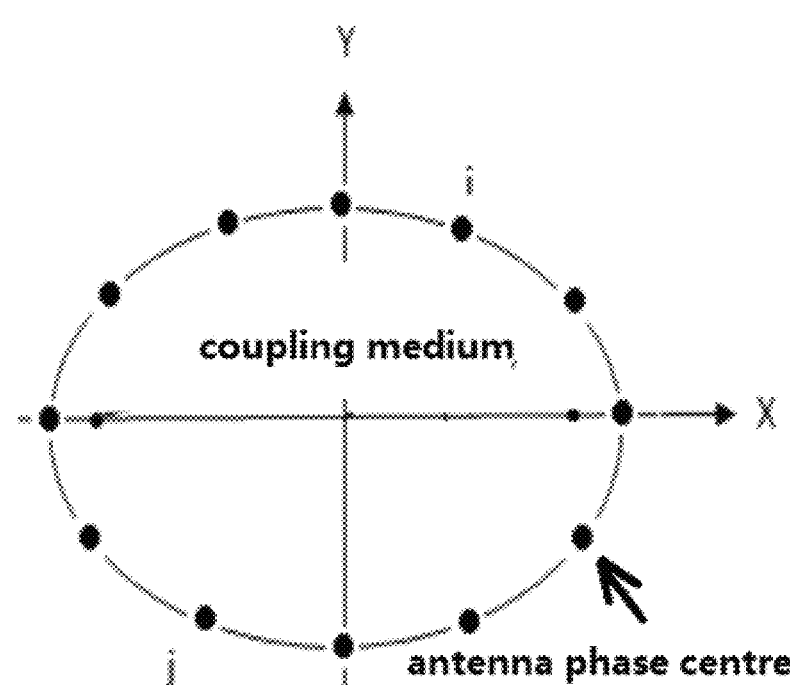
FIG. 3b is a schematic diagram of an antenna array filled with a coupling medium for the calibration process.
Figure 5:
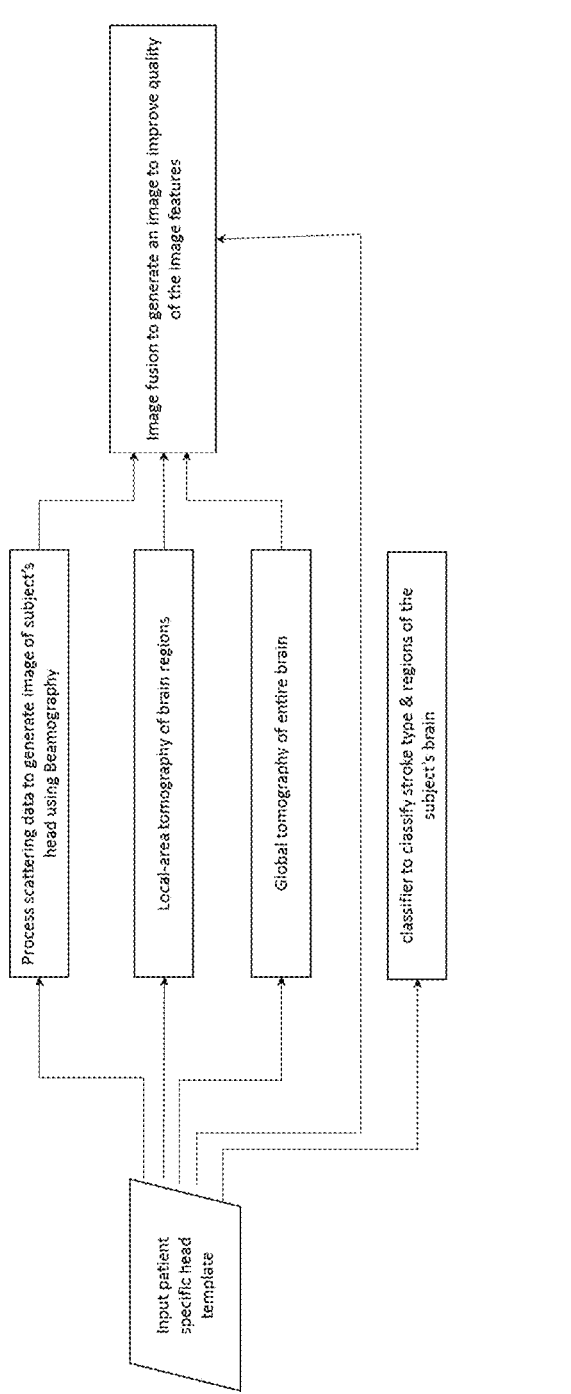
FIG. 5 is a flow diagram showing the generation of a fused image from a patient specific head template within in the imaging process of FIG. 3.

Step #2: Insert a homogeneous and low-loss coupling medium within the imaging domain, as shown schematically in FIG. 3b. The shape of this coupling medium should match the shape of the antenna array, and its permittivity value should be close to the average value of the imaged object, in the described embodiment being the human head. Then, use the N-port VNA 104 to record the $S_{ij}$(f) (i≠j) data. In this case, we have:

$$S_{ij}(f) = \alpha G_i(f) G_j(f) U_{ij}(f)$$

$$s_{jk}(f) = \alpha G_j(f) G_k(f) U_{jk}(f)$$

$$\left|\frac{G_i(f)}{G_k(f)}\right| = \left|\frac{S_{ij}(f)}{S_{jk}(f)}\right| * \left|\frac{U_{jk}(f)}{U_{ij}(f)}\right|$$

where U(f) represents the coupling coefficient for the antenna elements in a specified propagation model, which is independent of the characteristics of the individual antennas. It is a different concept to antenna mutual coupling. The value of the coupling coefficient ratio ($|U_{ij}(f)/U_{jk}(f)|$) can be determined in an analytical manner and calculated in the ideal simulation environment by assuming that the gains of all point sources are identical ($G_1(f) = G_2(f) = . . . = G_N(f)$), in which case:

$$\left|\frac{U_{ij}(f)}{U_{jk}(f)}\right| = \left|\frac{\overline{S_{ij}}(f)}{\overline{S_{jk}}(f)}\right|$$

where $\overline{s}(f)$ is the coefficient determined from the simulation.

The aforementioned calibration process determines the phase and amplitude differences between different RF channels in the system. If channel-1 is nominated as the reference channel, then the following transformation function is used to correct the measurement data to be used by the post-processing algorithms.

$$\text{Corr}_{ii}(f) = \left|\frac{G_1(f)}{G_i(f)}\right| * Meas_{ii}(f) * \exp\{P_1(f) - P_i(f)\} \quad i = 1, 2, \ldots, N$$

$$\text{Corr}_{ij}(f) = \left|\frac{G_1(f)}{G_i(f)}\right| \left|\frac{G_1(f)}{G_j(f)}\right| Meas_{ii}(f) * \exp\{P_1(f) - P_i(f) - P_j(f)\}$$

$$i, j = 1, 2, \ldots, N, i \neq j$$

Having generated the calibration data for the antenna array at step 302, the system can be used to scan the object to be imaged. To facilitate the process, a template generation process 400, as shown in FIG. 4, is executed to generate an input template 416 of the object by machine learning.

Template Generation (400)

The template generation process 400 estimates internal information about the object based on external and known properties about the object, as well as structure learned from a large number of samples of MRI and/or CT-based information. The goal of this is to provide a map of, in the described embodiment, the spatial distribution of different head tissues. The template generation process 400 begins at step 402, as shown in FIG. 4, by acquiring data representing the head surface and biodata for the subject whose head is to be scanned by the system. Specifically, the subject's age, gender and weight (in addition to ethnicity and height, if available) are determined and entered into the system by a user. At step 406, the system generates subject head data representing the outer shape of the subject's head. In the described embodiment, this is done by using a 3D camera 108, as shown in FIG. 1, to generate a three-dimensional (3D) surface of the subject's head. A wig cap or similar, can be used to keep the subject's hair down. Alternatively, the subject head data can be estimated using the antenna array itself to measure the outer boundary of the subject's head.

At step 408, the system uses the subject's biodata and 3D scanned surface of the subject's head to provide a base-template. The selection is made using one of the following three options:

1. use a previous scan of the actual subject's head as a template;
2. use a template library and find the closest head to the current subject through nearest neighbour (based on patient biodata & head surface); or
3. directly predict the most likely head using machine learning (based on patient biodata & head surface).

In Option 1, a prior brain scan of the subject is used. The scan data is converted to a suitable electromagnetic format by performing tissue segmentation and then tissue property assignment (to assign values of permittivity and conductivity to the different tissues identified by the tissue segmentation).

In Option 2, the system automatically selects a corresponding head template from a database of head templates that is either stored locally on the system, or is accessed remotely via the Internet, such that the stored head template whose biodata and surface most closely matches the biodata of the subject is selected as an initial head template for the subject. In the described embodiment, this is done using a standard machine learning method such as regression or nearest neighbour classification, known to those skilled in the art.

In Option 3, a developed machine learning model that takes as input the surface of the head and the biodata, and directly learns and predicts a template head without a template library. This works by training a machine learning model such as a deep neural network to learn the values that the head can take and how these vary depending on the input. This can be achieved through a feed-forward deep neural network, or through generative models such as Generative Adversarial Networks (GANs) or Variational Auto-Encoders (VAEs).

Preparation of the Templates

In the described embodiment, the head templates are generated from MRI data as this provides a large source of data for modelling, as well as high resolution tissue distribution. In MRI, different intensity values correspond to different tissues based on their magnetic properties. This needs to be converted into a useable format for electromagnetic imaging, and the MRI to EM conversion is performed as follows:

1) First segment the MRI/CT data into different tissues. The orientation and intensity of the scans are first normalised (e.g., through Bias Field Correction), and the brain is then segmented into a brain region and a non-brain region. Next, segment the brain region into three tissue types (grey, white, and CSF (cerebro-spinal fluid)) based on intensity values and using a multi-tissue segmentation algorithm such as Fuzzy-C-Means clustering or FAST, and similarly segment the non-brain region into a skull region and a skin region. A deep neural-network approach such as a 3D U-Net can also be used, and multiple modalities can be utilised to improve the segmentation.

2) Assign tissue values to the different tissues based on a table of dielectric properties at the desired frequency of imaging.

Each template represents a two or three-dimensional model of the human head, defining the spatial and dielectric properties (permittivity and conductivity values) of the various tissues of the head, including the skin, skull, cerebro-spinal fluid (CSF), white matter and gray matter of the brain. This effectively forms a map of pixels (2D) or voxels (3D) with values corresponding to the dielectric properties (permittivity & conductivity) of the corresponding tissue.

Having determined the three-dimensional shape of the subject head and corresponding base head template, the base head template selected at step 408 is transformed or 'warped' so that its outer surface matches the measured shape of the subject's head. In the described embodiment, this is first done by warping landmark points between the base-head-template and the true patient's head surface according to the following surface-based-registration process.

Firstly, the locations of the patient's anatomical landmarks or "fiducials": Nasion (NAS), and left and right pre-auricular points (LPA and RPA accordingly) are determined. This can be achieved using a digitiser, or by manually placing markers on these three locations and using computer-vision-based marker-detection, or they can be manually labelled using the system's computer interface. These anatomical landmarks or "fiducials" enable the scanned surface to be transformed to normalised coordinates where the positive X, Y and Z will go through NAS, LPA and top of the head, respectively.

Landmark localisation: instead of following popular configurations of 10-20 or 10-5 which are used in EEG, a denser set of landmarks is generated, where the landmark points are extracted based on the fiducials and the 3D head surface. From the fiducials, several planes are created, and the intersection between the planes and the head surface gives the landmark positions. The number of landmark points selected depends on the desired density and accuracy, and in general a larger number of points allows for higher accuracy. This process of landmark localisation is performed automatically.

Warping is the process of mapping from measured surface presented via landmark points to an example of a head, in order to predict the anatomical structure of measured head. In the described embodiment, this is done using Thin Plate Spline (TPS) warping, although an elastic warping method may be used as an alternative in other embodiments. The resulting data is then re-sampled to a uniform grid and converted to an appropriate format for the imaging algorithms (e.g., converted to a CAD model).

To facilitate use of the template with data generated from the actual subject, consistent coordinates are needed between the template and the patient (i.e., voxels need to be in the same position in 3D space so that they can be directly compared). In the described embodiment, this is achieved by matching the antenna sensor positions to the fiducials (using the 3D camera 108).

The machine learning model of "Option 3" is iteratively trained to predict the head, and there is an associated error or cost function which needs to be optimised. This cost is the difference between the machine learning model's predicted template and the true patient head. A good model will predict a model that has a low cost, i.e. it predicts a template head that is very similar to the true head. The model can then be applied to new unseen heads not in the training data set.

The generation of accurate head templates as described above allows the imaging and classification processes described herein to generate clearer and higher quality images of the brain, and significantly improves the accuracy of brain stroke diagnosis.

Returning to the flow diagram of FIG. 3, at step 306 the subject's head is scanned by the system. That is, the analysis component 106 instructs the VNA 104 to sequentially energise the antennas of the antenna arrays inside the antenna platform (Headset) 116 so that they generate and transmit electromagnetic waves in the form of microwave signals into and through the subject's head so that they can be scattered by features within the subject's head, and the scattered signals detected by each of the antennas of the antenna array inside the antenna platform 102, and the corresponding signals sent to the VNA 104 for processing to generate corresponding S-parameters.

The detection capability, image resolution, and accuracy of the system and process described herein depend upon the performance of the antenna array, and the compactness and portability of the system depends on the size and weight of the antenna array and the antenna assembly 102 of which the antenna array is a part. The antenna array is an array of individual antenna elements that have wideband and unidirectional electromagnetic characteristics, with a high front-to-back ratio (FBR), while also being compact with a low profile. These electromagnetic characteristics ensure high penetration depth of the EM waves into the human head tissues, resulting in a high signal to noise ratio (SNR) that enhances the useful reflected signal from features of interest (e.g., a stroke) inside the brain. The antenna assembly 102 and its array of imaging antennas described below meet these requirements.

The antenna array can be provided in any of several forms, including as a flexible array or a matched loaded waveguide array.

To avoid strong clutter effects in the received microwave signals (which can cause artefacts in the final images), the antennas' mutual coupling and head skin/hair reflections are minimized or at least reduced by providing the antennas in the form of dielectric-loaded tapered or corrugated waveguide antennas.

The antennas have a proper flexible coupling pads between their ends and the imaged head. Moreover, they should be partially or totally surrounded by a lossy decoupling medium. For best matching between the antennas and the head, the coupling medium inside the antennas, and the pad between the antennas and the head, are formed from a mixture materials (epoxy resin plus aluminium powder, or polyester resin plus aluminium power for the coupling medium and Cyano-resin CR-V plus ceramic powder for the flexible pads) to have appropriate dielectric properties (a dielectric constant of 40-50, and a loss tangent less than 0.1 at 0.7 GHz), whereas the decoupling medium surrounding the antennas is composed of a mixture of materials (Cyanoresin CR-S or Cyanoresin CR-U with graphite powder and carbon powder) so as to have a high dielectric constant of more than 60 and high loss tangent of more than 1 at 0.7 GHz. The whole antenna array should be surrounded by an absorber to shield the system from the effects of the surrounding environment and to absorb any stray scattered fields from the imaged head. The antenna array can be fixed, or movable. In the latter case, the imaging domain will be variable in size, and in this case a suitable tool, such as position sensors, should be used to determine the exact locations of the antennas as required for the data processing and imaging processes.

For successful image reconstruction, the relative locations of the antennas arranged around the subject's head need to be known to determine the corresponding time delays of the scattered microwave signals. When the headset is worn by a subject, the antenna array becomes generally conformal with the subject's head, but the antennas can still have different orientations and distances relative to the subject's head. In view of this, the system uses the 3D contour of the subject's head acquired from step 406 of the Template Generation Process and the known antenna array configuration to calculate the spatial location and orientation of each antenna, specifically the excitation port of each imaging antenna, and this constitutes a priori information that is provided to the s-parameter processes described herein.

The process of determining relative distance and orientation of the antenna array includes using fiducials found at step 406, especially the centre point, i.e., Nasion, to align the headset to the correct location before the system is operated. Since the information of the antenna configuration in the headset is known, thus by using the 3D head surface acquired at step 406, each antenna's relative distance and its orientation towards the subject's head is determined.

Image Generation 306/308

Having scanned the head at step 306, the resulting scattering data is processed to generate one or more two- or three-dimensional images of the patient's head using an image generation process 308 that combines the benefits of radar beamforming and tomography, and that the inventors therefore refer to as 'beamography'. In particular, the use of this new process reduces the time required to process the scattering data and generate the images, which is an important benefit in emergency situations.

By way of overview, the image generation or 'beamography' process 308 executed by the system utilizes the measured multi-static scattering parameters of the imaging antennas that surround the imaged object to generate two or three-dimensional images. It also utilizes the measured scattering parameters of the antennas when the imaging domain is either filled with a matching medium or contains a phantom emulating an average human head to calibrate the signals measured from the subject's head.

An average-trace subtraction method, in which the average measured value (over all signals) is subtracted from each signal at each frequency sample, is used to remove strong reflections and clutter from the scattering data. As a priori information, the effective dielectric properties of the wave-propagation path inside the imaged domain as seen by each antenna with respect to each voxel of the imaged domain is estimated using a shortest-path-finder technique and an estimated permittivity model (template) of the healthy subject.

The processed data are then virtually back-propagated to the imaged domain by considering the estimated dielectric properties of the object to estimate the power intensity of tissues inside the domain. The spatial distribution of scattered power intensity within the imaged domain (also referred to herein for convenience as a "map" or "profile") is created at each frequency step by using the estimated dielectric properties from the healthy template and a simplified Green's function. The spatial distributions of power intensity for different frequencies are then superposed to generate an image that reveals abnormalities (if any) in the imaged domain. To determine the dielectric properties of an abnormality, an iterative computational procedure is used to update the dielectric permittivity values of the healthy template, and the updated properties are in turn used to recalculate the power intensity. Comparison of the power intensity of each pair of consecutive iteration steps and updating the permittivity map continues until a suitable accuracy criterion is met (e.g., when the difference in values between successive iterations is less than the threshold value).

a) Calibration 702

Figure 7:
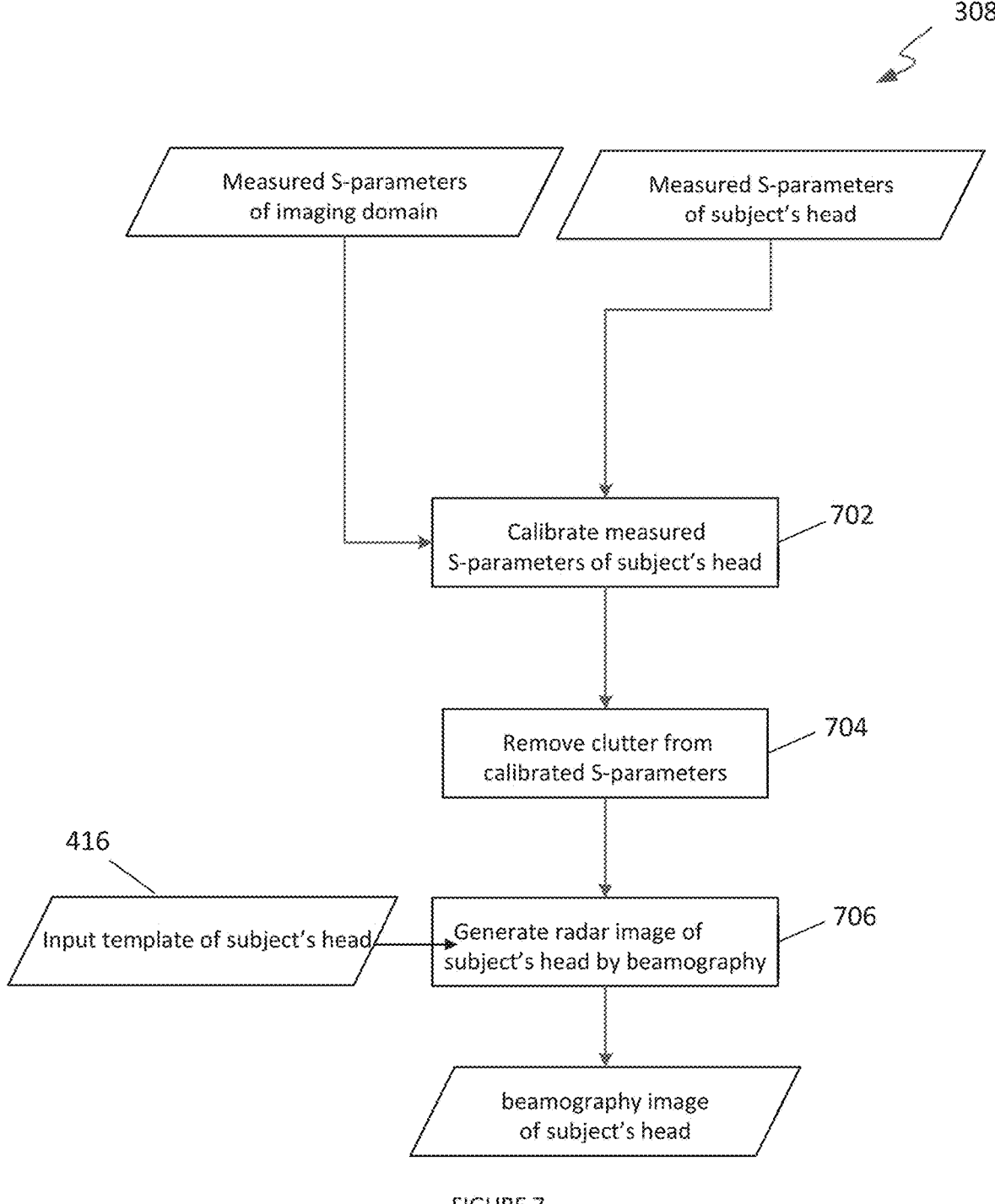
FIG. 7 is a flow diagram of an image generation process of the imaging process of FIG. 3.

The image generation or beamography process 308 is now described in more detail. As shown in FIG. 7, the image generation process 308 begins at step 702 by calibrating the measured scattering parameters of the subject's head, using measured scattering parameters of the imaging domain; that is, in the absence of the subject's head, and with the imaging domain filled by a material with dielectric properties of the matching medium or the average head phantom. The calibration process also mitigates the effects of any mismatch between the antennas, due to antenna manufacturing and assembling variations or errors, for example.

The calibrated data $$S_{mn}^{cal}$$

are obtained by dividing the scattering parameters $s_{mn}$ for scattering from the subject's head in the imaging domain by the scattering parameters $$S_{mn}^{b}$$

from the background matching medium (or calibration object such as a phantom head), as follows:

$$S_{mn}^{cal} = \frac{S_{mn}}{S_{mn}^{b}} \quad m, n = 1:Na \tag{1}$$

Where, m and n are receiver and transmitter indices, and Na represents the number of imaging antennas.

In some embodiments, logarithms of the data are used, as follows:

$$S_{mn}^{cal} = \log\left(\frac{S_{mn}}{S_{mn}^{b}}\right) = \log(S_{mn}) - \log(S_{mn}^{b}) \quad m, n = 1:na \tag{2}$$

Using logarithms of the scattering parameters allows the amplitude and phase differences of the data to be compared rather than its real and imaginary parts. In this way, the phase variation information useful for the retrieval of dielectric properties of the subject's head is retained. In addition, the scattering data from different antennas become symmetric and suitable for clutter removal in the next step of the imaging process.

b) Clutter Removal 704

The contrast between the dielectric properties of the outer layers of the subject's head (or other medical object to be imaged) causes a large portion of the wave to be reflected back to the transmitting antenna, and these reflections are typically strong enough to mask reflections from deeper tissues. Consequently, reflections from the outer layers should be removed or at least considerably mitigated to allow the detection of features of interest within the imaged object. The reflections can be mitigated by any suitable approach, including standard methods known to those skilled in the art, such as Average Trace Subtraction, Spatial Filtering, Subspace Projection, Differential Approach, or Hybrid Clutter Rejection, for example. In the described embodiments, a combination of average subtraction and differential approach is utilized to remove the strong reflections or 'clutter' from the calibrated data at step 704, as follows.

If the distance between each of the antennas and the outer layer of the object (i.e., the skin of the subject's head) is constant, then the contributions of signals arising from outer reflections will be similar for all of the antennas, and these reflections can be separated by removing a constant value from the received signals. The average subtraction process, which subtracts a calculated average value from the received signals, can effectively mitigate reflections in this scenario. However, with the waveguide antennas it is usually impractical to provide uniform distances between the antennas and the skin of the subject's head. Nevertheless, the clutter removal process described below can be applied to signals from antennas with similar distances, such as 0-10 mm, to the skin. Specifically, the antenna signals are categorized based on their distances to the skin (or outer layer if the object to be imaged is not a human head) and the average of all the received signals in each category Ci is subtracted from the corresponding signal of the antenna at each frequency step:

$$S_{mn}^{cr} = \begin{cases} S_{mn}^{cal} - \frac{1}{n_a}\sum_{n=1}^{n_a} S_{nn}^{cal} \\ S_{mn}^{cal} - \frac{1}{n_a(n_a-1)}\sum_{\substack{m,n=1 \\ m \neq n}}^{n_a} S_{mn}^{cal} \end{cases} \quad n \in C_i, i = 1:N_c \tag{3}$$

where, $$S_{mn}^{cr}$$

represents the clutter-removed signal, and Nc is the number of categories. In the multi-static configuration of the described embodiments, the clutter removal process is applied to the calibrated reflection $$\left(S_{nn}^{cal}\right)$$

and transmission signals $$\left(S_{mn}^{cal}\right)$$

separately, as defined in Equation (3) above. This clutter removal process 704 estimates the reflection by averaging the signals from antennas with similar distances to the subject's head, instead of through inverse scattering. In addition, applying average subtraction for every frequency step enables this process to account for the frequency dependence of electromagnetic wave penetration depth.

c) Beamforming 706

Figure 8:
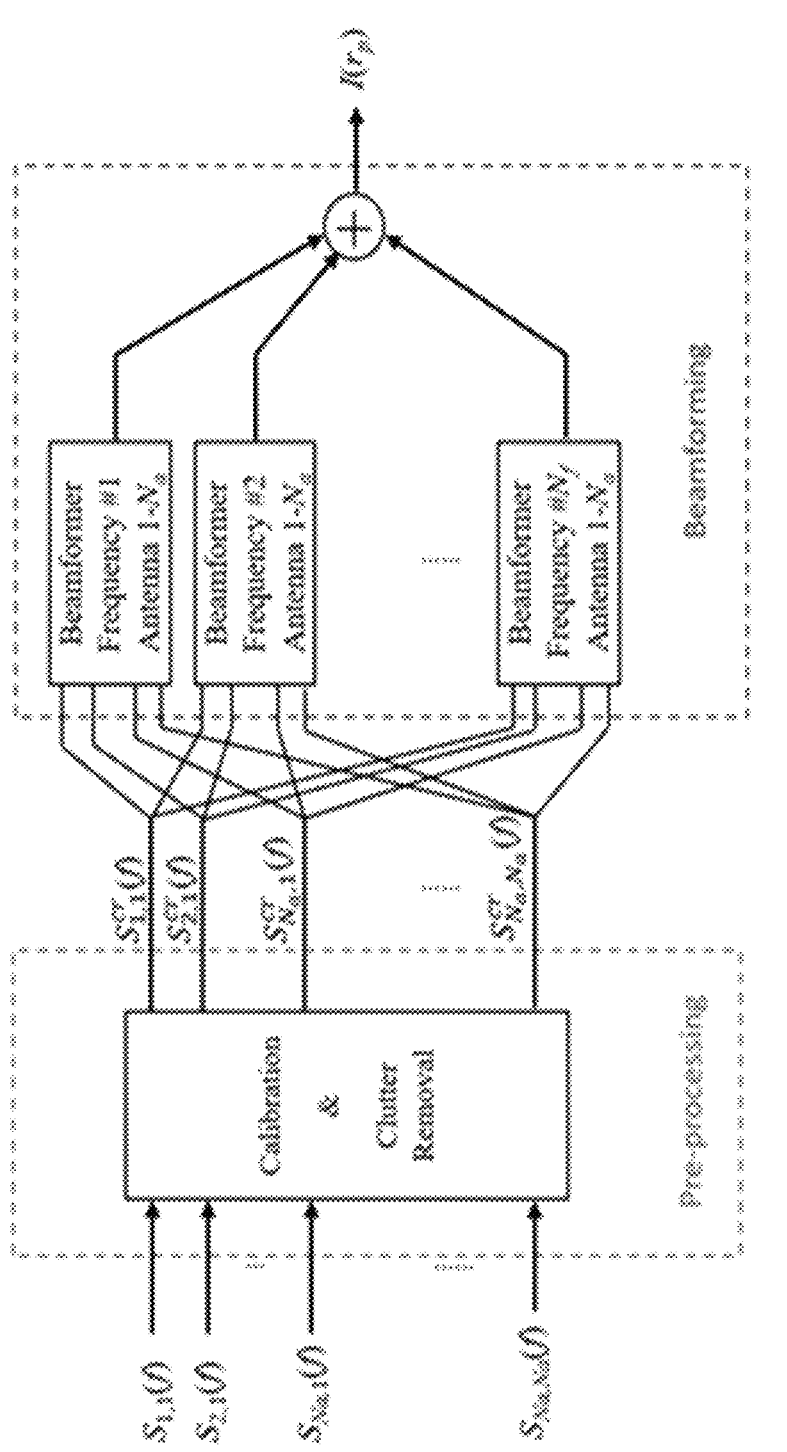
FIG. 8 is a functional block diagram of a beamography component of the analysis component of FIG. 2.
Figure 9:
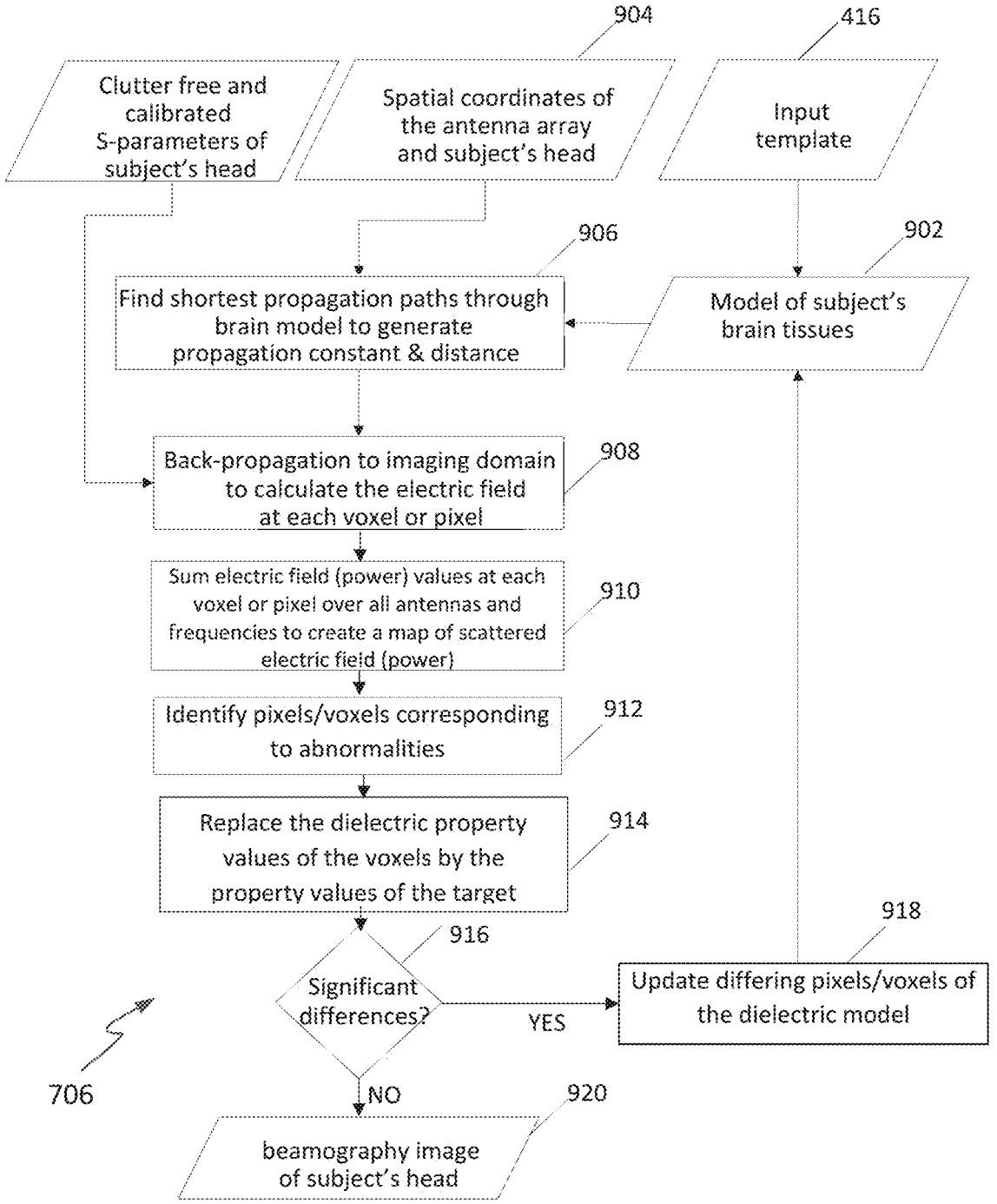
FIG. 9 is a flow diagram of a beamography process of the image generation process of FIG. 7.

By eliminating the boundary reflections, the imaged domain can be considered as a homogeneous medium. At step 706, the clutter-free and calibrated scattering parameters are passed through a frequency-domain beamformer, as shown in FIG. 8, to image the received signals as a function of location. In the beamography process, as shown in FIG. 9, the scattered power intensity in the imaged region is calculated by solving Maxwell's equations, and the total power is estimated by summing the calculated power intensities over all frequency samples and antenna positions. As a consequence of the significant permittivity contrast between healthy and unhealthy tissues, regions of high energy levels in the resulting image correspond to unhealthy tissues.

Figure 10:
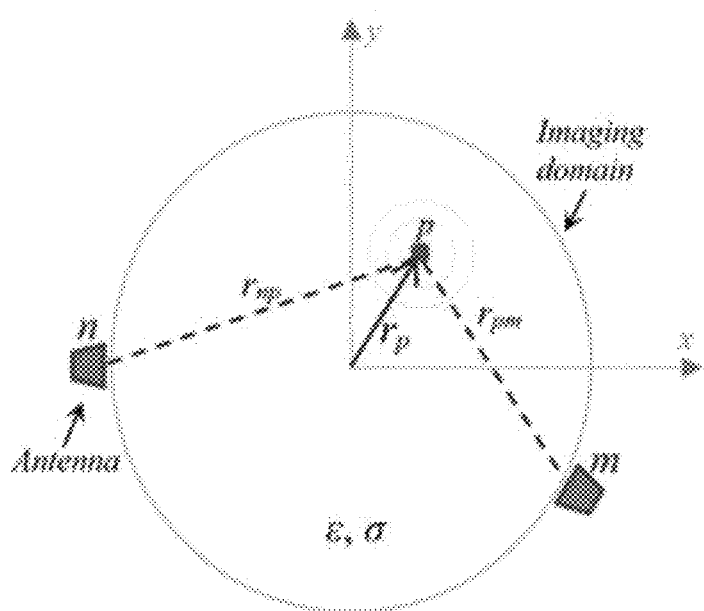
FIG. 10 is a schematic diagram illustrating the transmission of a microwave signal from a transmitting antenna into an imaging domain, the scattering of the microwave signal within the imaging domain, and the detection of the scattered signal by a receiving antenna.

A schematic representation of the imaging domain is shown in FIG. 10, where an electromagnetic wave is propagated from a transmitter n to an object that has unknown dielectric properties (conductivity ε and permittivity σ). The scattered field from different point scatterers inside the imaged domain is then measured by antenna m, outside the boundary of the imaging domain.

In the beamography process 706, the electric field Ep at the location of a point-scatterer p is calculated by estimating the electric fields at the location of the scatterer. To that end, the target response at each receiving antenna is correlated with the incident field and synthetically back-propagated to the imaged domain. The electric field at the location of the scatterer is then calculated as follows:

$$E_p = \frac{E_m}{E_n}G(\gamma r)e^{-\gamma r} = S_{mn}G(\gamma r)e^{-\gamma r} \tag{4}$$

where G is the two or three-dimensional Green's function of the point scatterer, r=|rnp|+|rpm| is the distance from the transmitting antenna to the point scatterer and then to the receiving antenna, and y is the propagation constant of the medium that the wave passes through, and is calculated by:

$$\gamma = \sqrt{j\omega\mu(\sigma + j\omega\varepsilon)}, \tag{5}$$

in which $j=\sqrt{-1}$, $\omega=2\pi f$ is angular frequency, μ is the permeability, and σ and ε are the conductivity and permittivity of the wave propagation path, respectively.

The point-scatterer electric field Ep is different from the scattering field $E^{scat}$ that is usually separated from the incident field in conventional electromagnetic estimations ($E_m=E^{scat}+E^{inc}$). However, in the processes described herein, Ep represents the sum of the scattering and incident fields at the location of point scatterer:

$$E_p = E^{scat}(r_p) + E^{inc}(r_p) \tag{6}$$

and $$E_m = \int_{dv} E_p dv \tag{7}$$

The electric field at a far-field distance from the scatterer r (r>2D2/λ, where D is the diameter of the point scatterer and λ is the effective wavelength inside the imaged domain) behaves as a spherical wave and uniform plane wave equations are governed. Therefore, the Maxwell's equation corresponding to Equation (4) is:

$$\nabla^2 G - \gamma^2 G = 0 \tag{8}$$

The differential equation corresponding to the radial part G(r) of the ansatz is the Bessel differential equation:

$$\frac{d^2}{dr^2}G(\gamma r) + \frac{1}{r}\frac{d}{dr}G(\gamma r) + \left(\gamma^2 - \frac{1}{r^2}\right)G(\gamma r) = 0, \tag{9}$$

where the solutions in complex form are given by:

$$H_i^{(1)}(\gamma r) = J_i(\gamma r) + jN_i(\gamma r) \tag{10}$$

$$H_i^{(2)}(\gamma r) = J_i(\gamma r) - jN_i(\gamma r) \tag{11}$$

which are the i-th order Hankel functions of the first and second kind, and J and N are Bessel functions of the first and second kind, respectively. Hankel functions are singular due to the presence of the singularity of the Bessel function of the second kind, also known as the Neumann function.

$$H_i^{(1)}$$

describes radially symmetric cylindrical waves traveling away from the scatterer (scattering fields), while the Hankel function of the second kind $$H_i^{(2)}$$

represents waves traveling towards the scatterer (incident fields). Considering the scattering field as a reflected wave due to the mismatch between the dielectric properties of the scatterer and the wave propagation path, both scattering and incident fields exist at the location of point scatterer with the same frequency and amplitude, and consequently the singular Neumann functions cancel out in superposition. Therefore, the solution is given by:

$$G(\gamma r) = \left[H_i^{(1)}(\gamma r) + H_i^{(2)}(\gamma r)\right] = 2J_i(\gamma r) \quad i > 0 \tag{12}$$

Following clutter removal, the first order (i=1) Bessel function is the dominant mode, and provides the best solution. Hence the point-scatterer field can be calculated by assigning the Green's function from Equation (12) into Equation (4):

$$E_p = 2S_{mn}J_1(\gamma r)e^{-\gamma r}, \tag{13}$$

where the Bessel function J1(γr) can be replaced with its polynomial approximation:

$$J_1(\gamma r) = \sum_{i=1}^{n} \frac{(-1)^{i+1}(2n)^{1-2i}(i+n-1)!}{(i-1)!\,(n-i)!\,i!}(-j\gamma r)^{2i-1} = \qquad (14)$$

$$\frac{1}{\pi}\sum_{i=0}^{n}\cos\left[\frac{\pi}{n}i \mp j\gamma r\sin\left(\frac{\pi}{n}i\right)\right],\, n \ge \frac{\gamma r}{2} \qquad 5$$

The point-scatterer field when the imaging domain is filled by the matching medium, $$E_p^b$$

can also be calculated by:

$$E_p^b = 2S_{mn}^b J_1(\gamma_b r)e^{-\gamma_b r}, \qquad (15)$$

where $\gamma b$ is the propagation constant of the background, and $$S_{mn}^b$$

is the measured scattering parameter of the background.

In the calculation of the point-scatterer field, the scattering field is considered as a reflected wave, which is superimposed on a forward wave in the background medium. Therefore, the reflection coefficient associated with the scatterer can be defined as:

$$\Gamma^{scat} = \left(\frac{S_{mn}}{S_{mn}^b}\right)\frac{J_1(\gamma r)e^{-\gamma r}}{J_1^*(\gamma_b r)e^{\gamma_b r}} = S_{mn}^{cr}\frac{J_1(\gamma r)}{J_1^*(\gamma_b r)}e^{-(\gamma+\gamma_b)r} \qquad (16)$$

where * represents the conjugation operation. Therefore, the scattering field at the location of point scatterer due to the wave transmitted by the n-th antenna and received by m-th antenna is given by:

$$E^{scat}(r_p) = E_n\Gamma^{scat}(r_p) = E_n S_{mn}^{cr}\frac{J_1(\gamma r)}{J_1^*(\gamma_b r)}e^{-(\gamma+\gamma_b)r} \qquad (17)$$

In a multi-static imaging configuration in which Na antennas act as both transmitters and receivers, the total power density ("density" because it is calculated per pixel area or voxel volume) generated by all of the antennas at the location of each scatterer is calculated to estimate the locations of any abnormalities. To that end, the total power density is calculated by summing the estimated electric fields inside the imaged object from different transmitters and receivers around the object, as follows:

$$P_{total}^{scat}(r_p) = \left|\frac{1}{N_a^2}\sum_{m=1}^{N_a}\sum_{n=1}^{N_a} S_{mn}^{cr}\frac{J_1(\gamma r)}{J_1^*(\gamma_b r)}e^{-(\gamma+\gamma_b)r}\right|^2 \qquad (18)$$

The incident field En is usually chosen to be one (volt/meter), thus, it is neglected in the calculations in Equation (18). To compensate for the lack of discrete observation points, different scattered profiles for different frequencies are superposed to generate an electromagnetic power image, as follows:

$$I(r_p) = \frac{1}{N_f N_a^4}\sum_{f=1}^{Nf}\left|\sum_{m=1}^{N_a}\sum_{n=1}^{N_a} S_{mn}^{cr}\frac{J_1(\gamma r)}{J_1^*(\gamma_b r)}e^{-(\gamma+\gamma_b)r}\right|^2 \qquad (19)$$

where Na and Nf are the number of antennas and frequency samples, respectively.

The average electric field at the point-scatterer can also be calculated by:

$$E_{avg}^{scat}(r_p) = \frac{1}{N_f N_a^2}\sum_{f=1}^{Nf}\sum_{m=1}^{N_a}\sum_{n=1}^{N_a} S_{mn}^{cr}\frac{J_1(\gamma r)}{J_1^*(\gamma_b r)}e^{-(\gamma+\gamma_b)r} \qquad (20)$$

In this case, the real part, imaginary part, and/or the phase of the average field $$E_{avg}^{scat}$$

can be used as the final image.

For the sake of completeness, the described process can also be used in monostatic measurement configurations by changing the triple summation operator to a double sum in Equation (19) and (20), as follows:

$$I^{mono}(r_p) = \frac{1}{N_f N_a^2}\sum_{f=1}^{Nf}\left|\sum_{n=1}^{N_a} S_{nn}^{cr}\frac{J_1(\gamma r)}{J_1^*(\gamma_b r)}e^{-(\gamma+\gamma_b)r}\right|^2 \qquad (21)$$

$$E_{avg}^{mono}(r_p) = \frac{1}{N_f N_a}\sum_{f=1}^{Nf}\sum_{n=1}^{N_a} S_{nn}^{cr}\frac{J_1(\gamma r)}{J_1^*(\gamma_b r)}e^{-(\gamma+\gamma_b)r} \qquad (22)$$

The described process can also be used to generate 3D images by using a 3D antenna array configuration around the imaged object. In that case, the point scatterer location rp represents a 3D vector in the volume of the imaged object. The 3D antenna array can be created by adding more rings of antennas above and/or below the 2D imaging plane, or by moving the antennas along the z-direction to scan the entire object. In either arrangement, an interpolation technique is used to generate 3D images or multi-slice images of the object.

Although the process described above does not provide a detailed image of dielectric properties, it does show regions of contrast in the dielectric properties, which is sufficient for the rapid detection of significant scatterers and their approximate locations. If required, the process can be extended to generate detailed images, as described below.

An important aspect of the beamography process 706 relates to the calculation of the propagation constant to be used in Equations (19) and (20). The average dielectric properties of the imaging domain can be used in the propagation model. However, in order to create more accurate images of heterogeneous objects, such as a human body, a more accurate estimated spatial distribution of dielectric properties in the imaging domain is required.

Due to the multiple reflections and refraction of the electromagnetic wave in a dispersive and heterogeneous environment, the wave passes through different tissues and follows different paths depending on the transmitter-receiver location with respect to the imaged object. In homogeneous environments, this path can be calculated as the direct (straight) path (shortest path) from each transmitter to the point scatterer, and from the point scatterer to each receiver. However, in heterogeneous media the electromagnetic wave follows the path with minimum propagation time or smallest delay. Consequently, the wave propagation path can be found at step 906 by finding the path with the minimum propagation time (t=γr/ω) inside the imaged object, providing the required values for the propagation constant and distance in Equations (19) and (20). To that end, a template that includes the anatomy and dielectric properties of the imaged object is deemed beneficial. This template can be the actual healthy model of the imaged object, extracted from images of other imaging modalities, such as MRI and/or CT devices, or an approximated one using the imaged 3D head contour 412.

A shortest-path-finder method is then utilized to find the wave propagation path inside the template. In the described embodiment of this process, the Dijkstra algorithm is utilised. By defining the propagation times (tuv) for the waves propagating from voxel v to its adjacent voxel u as the cost function, the shortest-path-finder algorithm finds the path with the minimal cost (propagation time) through the model. As a result, the location-specific propagation constant of the imaged domain seen by each transmitting-receiving antenna pair γmn (rp) is estimated. The propagation-distance parameter γr utilized in Equations (19) and (20) is then calculated by summing the γrs of all voxels along the propagation path from transmitter n to receiver m, as follows:

$$\gamma_{mn}(r_p)r_{mn}(r_p) = \Sigma_{uv \in r_{mn}(r_p)}\gamma_{uv}r_{uv}, \tag{23}$$

where, γuv and ruv are the propagation constant and distance from voxel v to its adjacent voxel u, respectively. The master equations of the imaging process are therefore:

$$I(r_p) = \frac{1}{N_f N_a^2} \Bigg| \tag{24}$$

$$\sum_{f=1}^{Nf}\left(\sum_{m=1}^{Na}\sum_{n=1}^{Na}S_{mn}^{cr}\frac{J_1(\gamma_{mn}(r_p)r_{mn}(r_p))}{J_1^*(\gamma_b r)}e^{-\gamma_{mn}(r_p)r_{mn}(r_p)-\gamma_b r}\right)^2\Bigg|$$

$$I^{mono}(r_p) = \frac{1}{N_f N_a} \tag{25}$$

$$\Bigg|\sum_{f=1}^{Nf}\left(\sum_{n=1}^{Na}S_{nn}^{cr}\frac{J_1(\gamma_{nn}(r_p)r_{nn}(r_p))}{J_1^*(\gamma_b r)}e^{-\gamma_{mn}(r_p)r_{mn}(r_p)-\gamma_b r}\right)^2\Bigg|$$

$$E_{avg}^{scat}(r_p) = \tag{26}$$

$$\frac{1}{N_f N_a^2}\sum_{f=1}^{Nf}\sum_{m=1}^{Na}\sum_{n=1}^{Na}S_{mn}^{cr}\frac{J_1(\gamma_{mn}(r_p)r_{mn}(r_p))}{J_1^*(\gamma_b r)}e^{-\gamma_{mn}(r_p)r_{mn}(r_p)-\gamma_b r}$$

$$E_{avg}^{mono}(r_p) = \tag{27}$$

$$\frac{1}{N_f N_a}\sum_{f=1}^{Nf}\sum_{n=1}^{Na}S_{nn}^{cr}\frac{J_1(\gamma_{nn}(r_p)r_{nn}(r_p))}{J_1^*(\gamma_b r)}e^{-\gamma_{mn}(r_p)r_{mn}(r_p)-\gamma_b r}$$

Another aspect relates to updating the model of the (e.g., healthy) subject's brain tissues (initially generated from or being the initial template) to estimate dielectric properties of the abnormality within the imaged object. The image created by Equations (22) or (23) shows the locations of significant scatterers (abnormalities). Therefore, the healthy model used in the initial step can be simply updated by changing the property values of the voxels that correspond to the abnormality locations. In this case, the location of an abnormality can be determined using any suitable technique, such as finding local maxima, thresholding, differential (subtracting subsequent images), clustering, and the like. In some embodiments, a thresholding process is utilized in which a histogram of the image generated by Equation (22) or (23) is generated, and the standard deviation of the histogram is taken as a threshold T. The location of an abnormality is then determined according to:

If I(voxel)>T, then voxel ϵ "unhealthy tissue", else voxel ϵ "healthy tissue"

After finding the locations of unhealthy tissues, the dielectric model is updated by replacing the permittivity and conductivity values of the voxels corresponding to the location of the abnormality in the model by the property values of the target. Alternatively, an optimization technique can be used to incrementally change the values of the healthy tissues according to:

$$\varepsilon_{new} = \varepsilon_{healthy} + \Delta\varepsilon, \ \sigma_{new} = \sigma_{healthy} + \Delta\sigma \tag{28}$$

The shortest-path-finder process is then performed on the updated template to calculate the new location-specific propagation constant. The new propagation constant is then substituted into Equation (22) or (23) to estimate the new scattering profile of the object. This iterative process is repeated until the updated values do not change substantially with respect to their values in the previous iteration, as shown in FIG. 9, indicating that the error has reached a small value.

An alternative stopping criteria for the iteration loop is to compare the calculated and measured electromagnetic energy in the antennas. When the antenna n transmits an electric field to the imaged object, it is scattered in the imaged domain and received by all of the antennas. Hence, the total electric fields received by the antennas around the object are the sum of scattered electric fields from different scatterers in the domain. Therefore, the total energy measured by all antennas can be compared to the calculated scattered energy to find the energy mismatch ΔS between the utilized template and the actual measured object, as follows:

$$\Delta S = \left| S_{total}^{meas} - S_{total}^{calc} \right| = \sum_{m=1}^{Na}\sum_{n=1}^{Na}S_{mn}^{cr} - \tag{29}$$

$$\sum_{p=1}^{Np}\sum_{m=1}^{Na}\sum_{n=1}^{Na}S_{mn}^{cr}\frac{J_1(\gamma_{mn}(r_p)r_{mn}(r_p))}{J_1^*(\gamma_b r)}e^{-\gamma_{mn}(r_p)r_{mn}(r_p)-\gamma_b r}$$

where Np is the number of scattering points in the imaged domain. The iterative process can then be utilized to minimize the energy mismatch ΔS through optimization.

By way of summary, the beamography process can be represented by the following steps, as shown in the flow diagram of FIG. 9:

Step 906: the input template 416 of the healthy object (in the context of the described embodiments, being the subject's head) defines the initial values of an updateable model 902 of the object; this model 902 and the locations 904 of the antennas relative to the subject's head are processed to calculate the location-specific propagation constant of the object by a shortest path finder method Step 908: the calibrated and decluttered scattering parameters of the object are back-propagated to the imaging domain to estimate the electric field at each pixel (or voxel, if 3D) within the imaging domain Step 910: the electric field power densities at each pixel (or voxel) (summed over all antennas) are calculated and summed over each transmitted frequency to generate a power density map or image of the object (i.e., representing the spatial distribution of scattered electric field power within the object)

Step 912: the pixel/voxel locations of any abnormality (significant scatterer) are determined (e.g., by using a thresholding technique)

Step 914: the model 902 is duplicated and a copy of that is updated by replacing the values of the pixels/voxels that correspond to the abnormality locations Step 916: a test is performed to determine whether there are any significant differences between the two models; if the test determined that there are significant differences between the models, then the process branches to step 918 below Step 918: the process loops back to re-calculate the propagation constant and distance at step 906 by using the updated model Otherwise, if the test at step 916 determined that there are no significant differences between the current model 902 and the most recently updated model, then the latter is output as the beamography image 920 of the object.

It will be apparent that the test at step 916 defines the termination or exit criterion of an iteration loop, and thus the beamography process 706 is an iterative process.

The power density map generated at step 910 shows the location of abnormalities in the brain. For example, a haemorrhagic stroke appears clear with a high intensity, whereas a clot appears as a lowest intensity region compared to its neighbouring tissue. A high intensity of a suspected region is an indicator that it is a bleeding region, whereas a missing abnormality or a low intensity while the symptoms of stroke persist indicates a blood clot.

The final beamography image 920 of the subject's head can either represent only the permittivity and/or the conductivity of the imaged region, or it can be updated to include data defining the locations of one or more tissue properties of interest, such as water content, and/or one or more relevant labels (e.g., whether tissue is abnormal, etc).

d) Optimisation

If required, the beamography process 706 can be sped up by decreasing the number of frequency samples, providing that this can be done without compromising (or overly compromising) image quality. To that end, the Nyquist theorem can be applied in the frequency domain to find the maximum frequency step (and thus minimum number of frequency samples) for reconstructive sampling. The Nyquist theorem is applied in the frequency domain in view of the time-limited feature of the received signals.

According to the Nyquist theorem, to theoretically be able to recover the whole data, the sampling step $\delta f$, should be less than $\frac{1}{2}\tau$, where $\tau$ is time-width of the time-limited signal. If the Nyquist criterion is not satisfied (undersampling), a portion of the data will be missed, causing overlapping of the reconstructed signals and resulting in an image with incorrect and/or multiple targets. Oversampling (sampling at a rate higher than the Nyquist rate) can improve the resolution and avoid overlapping, but requires additional time for the measurements and for processing. By considering the time-width of the received signals equal to the data acquisition time, and according to the signal bandwidth B, the minimum number of samples can be calculated as:

$$n_s > \frac{B}{\delta f} \qquad (30)$$

Using the minimum number of samples in the imaging process significantly reduces the processing time while maintaining accurate imaging.

The beamography process 706 described herein differs considerably from standard microwave tomography, which usually needs to solve ill-posed inverse problems to estimate the dielectric properties of the tissues. In comparison to time-domain methods (such as confocal, space-time beamforming MIST, and adaptive beamforming imaging methods), the beamography process 706 described herein is less computationally intensive, and performs all of its calculations in the frequency domain, making it more immune to noise and multiple reflections produced by multilayer structures.

The final beamography image 920 of the subject's head shows any abnormality in the brain. For example, a haemorrhagic stroke appears clear with a high intensity, whereas a clot appears as a lowest intensity region compared to its neighbouring tissue. A high intensity of a suspected region is an indicator that it is a bleeding, whereas a missing abnormality or a low intensity while the symptoms of stroke persist indicates a blood clot. The image can represent only the permittivity and/or the conductivity of the imaged region, it can be updated to include data defining the locations of one or more tissue properties of interest, such as water content, and/or one or more relevant labels (e.g., whether tissue is abnormal, etc).

Classification 312

The determination of whether a stroke is caused by bleeding or clots, as well as localising its position, are important in the diagnosis and treatment of acute strokes, and are also key issues in post-stroke management. In general, identifying stroke subtypes from an electromagnetic head scan system is based on image reconstruction algorithms. However, image-based methods are time-consuming and have low accuracy. Described below is a novel complex network approach applied to an electromagnetic scanning system to identify Intracranial Haemorrhage (ICH) from Ischemic Strokes (IS) and localize the stroke position. The classification is based on evaluating the difference between ICH and IS groups using graph degree mutual information (GDMI), where each subject consists of multi-channel antenna received signals. Each signal is converted into a graph to avoid different signal amplitudes. Then the relationship between each pair of graph degree features is calculated by mutual information and input to a support vector machine to identify the ICH from ICH. An accuracy of 95% is achieved in identifying ICH for IS. Regarding localization, weighted graphs are applied to extract the strength features between pairs of antennas from transmitter to receiver. The largest weighted pairs will be crossing the target. The execution time for graph feature extraction and classification or localization is less than one minute, which is suitable for a stroke emergency treatment system.

1. Summary of Methodology

FIG. 11 is a flow diagram of the data processing and analysis steps before classification and localization. In this case, the system workflow can be summarized as follows:

1. multi-channel input signals are received from the antenna array as shown in FIG. 1(*a*), where the default number of channels, N, is 16.

2. The scattered signals received from each antenna are frequency domain signals (magnitude and phase) or time series, where the number of sample points is greater than 700.

3. An inverse FFT is used to convert these signals to a multi-channel time series if the input is not already a times series.

4. Next, the multi-channel time series is mapped to N×N=16×16=256 graphs using the Fast Weighted Horizontal Visibility Algorithm (FWHVA) described in G. Zhu, Y. Li, and P. P. Wen, "Epileptic seizure detection in EEGs signals using a fast weighted horizontal visibility algorithm," Computer methods and programs in biomedicine, vol. 115, pp. 64-75, 2014.

5. The degree sequence and the weighted strength sequence is extracted as shown in FIG. 16(b).

6. Lastly, the output features: degrees and strength are used for classification and localisation, respectively.

FIG. 12 is a flow diagram of the classification process that follows the process of FIG. 11 FIG. 13 is a flow diagram of the localization process that follows the process of FIG. 11

2. Classification Methodology in Detail

To supplement the output images 920 which indicate whether a patient has a stroke, a classification process is performed to assess the stroke type using the S-parameters. In addition, a template and a fused brain image as described below can be used to improve accuracy. In general, features can be calculated by correlation, coherence, or synchronization algorithms and forwarded to general classifiers (such as SVMs, or random forests) or through deep learning neural networks to identify the subject as ICH, IS or healthy.

In the described embodiment, a complex network method is used at step 312 to assess the stroke type, using the measured S-parameters. The classification process 312 is able not only to differentiate between ICH, IS and healthy persons, but also to localize the stroke position.

FIG. 12 is a flow diagram of the classification process 312. The scattered field data (S-parameters) are collected from N antennas in the frequency domain, resulting in N×N signals. Then an inverse FFT converts the $N^2$ frequency domain signals into $N^2$ time series signals. Each time series signal ($X=x_1, x_2 \ldots, x_T$) is then mapped to a graph, $G(V;$ E), consisting of nodes/vertices (V) and edges (E). Specifically, the fast weighted horizontal visibility algorithm (FWHVA) is used to transform the data to a horizontal visibility graph (HVG), where each time point $x_i$ is a vertex of the graph, and the relationship between any two points ($x_i$; $x_j$) is represented as an edge $e_{i,j}$, where:

$$e_{i,j} = \begin{cases} 1, & x_i < x_k \wedge x_k < x_j, \forall\, k \in (i, j) \\ 0, & \text{otherwise} \end{cases} \quad (1)$$

where $e_{ij}=1$ indicates that an edge exists, a value of zero indicating that no edge exists. FIG. 16(b) shows a graph generated from the scattering parameters from a human head with IS from the second antenna, based on equation (1).

After each graph is constructed, node degree and degree sequence features are used to characterise the graph. The degree, $d(v_i)$, of node $v_i$ is the number of connected edges from $v_i$, and the degree sequence (DS) is a sequence of the graph degrees concatenated in order of node number, $[d(v_1), d(v_2), \ldots d(v_T)]$. For example, in the graph of FIG. 16(b), the degree, $d(1)=1$ and $d(2)=2$, while DS=(1; 2; 3; 5, . . . ; 2; 1).

Once the graphs are constructed, graph degree mutual information is computed between each pair of graphs. Mutual information (MI) is commonly used to measure a random variable's mutual dependence to another. Given two discrete variables X and Y, the mutual information of X and Y is given by:

$$MI(X, Y) = \sum_{y \in Y} \sum_{x \in X} p(x, y) \log\left(\frac{p(x, y)}{p(x)p(y)}\right) \quad (2)$$

where p(x) is the probability density of X, and p(x, y) is the joint probability distribution function of X and Y. In general, if X and Y are dependent, then MI is higher. In the described embodiment, instead of computing the mutual information between graphs, which is complex, the system uses a simpler and faster method referred to herein as graph degree mutual information (GDMI), which compares the degree sequences of two graphs. Given two degree sequences, DSx, DSy of two HVGs, Gx, Gy, the graph degree mutual information (GDMI) of the two graphs is measured as follows,:

$$GDMI(Gx, Gy) = MI(DSx, DSy) \quad (3)$$

If Gx and Gy are similar, the corresponding GDMI(Gx; Gy) is higher; otherwise, if Gx and Gy are different, the value is lower.

An $N^2 \times N^2$ matrix is obtained after every combination of graph degree sequences is inputted into equation (3). If the degree sequences of two graphs Gx and Gy are the same, then GDMI(Gx, Gy)=0 so that the diagonals of the GDMI matrix are always zero.

To classify the stroke type (bleeding/clot), a support vector machine (SVM) classifier is used. SVMs have been successfully used to classify HVG features associated with alcoholics and sleep EEG signals. They can perform both linear space discrimination and nonlinear classification by choosing different kernel functions which can be linear, polynomial kernel, radial basis function (RBF) or sigmoid. The described embodiment uses the SVM algorithm with an RBF kernel. A training set is first used to learn the decision hyperplane between the features of the two stroke types, and optionally the healthy case, using a multi-class SVM, and then is applied to classify the stroke type from new measurements.

The classification process 312 is fast and reliable as it normalizes the data for different head sizes. Currently, the computing speed is less than a minute (wall clock time) using a general-purpose computer. The classification process 312 can also localize the stroke based on the generated time series and antenna intersections, as described below.

3. Localisation Methodology in Detail

To perform localisation, the inventors noted that a brain containing a stroke has an imbalance in the transmitted/received signals. Assuming that the head is approximately symmetric across the major and minor axes (i.e., across the sagittal plane, separating the left-right of the brain, and across the central coronal plane, separating the front and back of the brain), symmetric pairs of antennas across these lines of symmetry should have similar signals within a healthy head. If symmetric pairs of antennas measure different signals, this indicates an abnormality such as a stroke, and this observation can be used to facilitate localisation.

FIG. 17 shows a cross-section of the brain surrounded by a 16-element electromagnetic-imaging antenna array, with pairs of antenna signals and a stroke 1702. Signals from the antenna pair (1-7) will be significantly different from its symmetric pair (1-11), due to only one of the signals crossing the stroke. However, the 1-13 and the 1-5 antenna pairs should have similar received signals. The largest weight pairs will be across the stroke target. Given a 16-element antenna array, the two approximate axes of symmetry of the brain correspond to signals originating from antennas 1, 5, 9 and 13.

To perform localisation, a weighted horizontal visibility graph (w-HVG) is computed. The procedure is as described above with the time series to unweighted graph conversion, but with an initial weight term, and the resulting graph is denoted as G(V, E, W). The weight $w_{i,j}$ of edge $e_{i,j}$ between nodes $v_i$ and $v_j$ (equivalently $x_i$ and $x_j$) is defined as follows:

$$w_{i,j} = \begin{cases} |(x_i - x_j)(i - j)|, & \text{if } e_{i,j} \text{ exists} \\ 0, & \text{otherwise} \end{cases} \tag{4}$$

A weighted graph is characterized by the concept of strength, where the strength of a node $v_i$ is defined as:

$$s_i = \sum_{j=1}^{T} w_{i,j} \tag{5}$$

For a weighted graph with T nodes, its mean strength is defined as:

$$\bar{s} = \frac{1}{T} \sum_{j=1}^{T} s_j \tag{6}$$

A differential weighted strength is defined as:

$$DW_{i,j} = \sum_{j=1}^{N} |\bar{s}\{i, j\} - Opp(\bar{s}\{i, j\})| \tag{7}$$

Where $\bar{s}$ is the mean strength between antennas 'i' and 'j', and Opp( ) indicates the symmetrically opposite antenna pair, originating from the same antenna i. For example, opposite antenna pairs when transmitting from antenna 1 or 9 include antennas 2-16, 3-15, 4-14, . . . , and opposite antennas when transmitting from antenna 5 or 13 include antenna pairs 1-9, 2-8, 3-7, . . . . It is noted that in realistic experiments, the antenna array might not be well calibrated. Accordingly, the bias in equation (7) can be removed as shown in equation (8):

$$DW_{i,j} = \sum_{j=1}^{N} |(\bar{s}\{i, j\} - ref_{ij}) - (Opp(\bar{s}\{i, j\}) - Opp(ref_{ij})|) \tag{8}$$

The pairs of antennas that cross a stroke target from the ith antenna can be detected using equation (9) below, where '%' refers to the modulus operator. Note that neighbouring antennas are not considered because the information gained from them is less than that from antennas spaced further apart.

$$\max \sum_{j=(i+4)\%16}^{(N/2+4)\%16} DW_{i,j} \tag{9}$$

When input signals contain signals from a brain template, the real position of the stroke can be obtained by computing geometric methods. Firstly, the intersection can be calculated based on equation (10), with four points of antenna positions (x1,y1), (x2,y2), (x3,y3) and (x4,y4).

$$p_x = \frac{\begin{vmatrix} x_1 & y_1 \\ x_2 & y_2 \end{vmatrix} \begin{vmatrix} x_1 & 1 \\ x_2 & 1 \end{vmatrix}}{\begin{vmatrix} x_3 & y_3 \\ x_4 & y_4 \end{vmatrix} \begin{vmatrix} x_3 & 1 \\ x_4 & 1 \end{vmatrix}} \Big/ \frac{\begin{vmatrix} x_1 & 1 \\ x_2 & 1 \end{vmatrix} \begin{vmatrix} y_1 & 1 \\ y_2 & 1 \end{vmatrix}}{\begin{vmatrix} x_3 & 1 \\ x_4 & 1 \end{vmatrix} \begin{vmatrix} y_3 & 1 \\ y_4 & 1 \end{vmatrix}} \tag{10}$$

$$p_y = \frac{\begin{vmatrix} x_1 & y_1 \\ x_2 & y_2 \end{vmatrix} \begin{vmatrix} y_1 & 1 \\ y_2 & 1 \end{vmatrix}}{\begin{vmatrix} x_3 & y_3 \\ x_4 & y_4 \end{vmatrix} \begin{vmatrix} y_3 & 1 \\ y_4 & 1 \end{vmatrix}} \Big/ \frac{\begin{vmatrix} x_1 & 1 \\ x_2 & 1 \end{vmatrix} \begin{vmatrix} y_1 & 1 \\ y_2 & 1 \end{vmatrix}}{\begin{vmatrix} x_3 & 1 \\ x_4 & 1 \end{vmatrix} \begin{vmatrix} y_3 & 1 \\ y_4 & 1 \end{vmatrix}} \tag{11}$$

However, Equation (9) cannot be enough to identify which hemisphere has the target, so a naive approach to detect whether the blood mass is in the left or right hemisphere is by comparing features (such as amplitude, mean degree or strength) from the left-hemisphere signals to those from the right hemisphere. However, this method can rarely provide a perfect answer due to the head not always being perfectly symmetrical. To address this difficulty, the process described herein uses the opposed pair of antennas 5 (left hemisphere) and 13 (right hemisphere) to detect whether the intersection should be placed on the left or right. The relevant process steps can be described as follows:

(a) Calculate the left intersection point, L0 (lx, ly), based on equation (10) and (11).

(b) Calculate the right intersection point R0 (rx, ry), based on equation (10) and (11).

(c) Draw a line segment from antenna 5 to an antenna, R1, on right side which is not the 13$^{th}$ antenna. The line segment will have the minimum distance to L0 apart from the 13$^{th}$ antenna.

(d) Pick up R1's neighbouring antenna, R2, whose line segment to antenna 5 is far away from L0 and R0.

(e) Calculate the difference weighted nodes w5$_r$ from 5$^{th}$ antenna to R1 and R2, respectively, where w5r=|S5r1−S5r2|

(f) Similarly for antenna 13, steps c to e are run to obtain the difference weighted nodes w13 from 13$^{th}$ antenna to two adjacent antennas L1 and L2, respectively (g) If w5$_r$>w13$_l$, then the intersection is in the left hemisphere, otherwise, it is in the right hemisphere.

Figure 21:
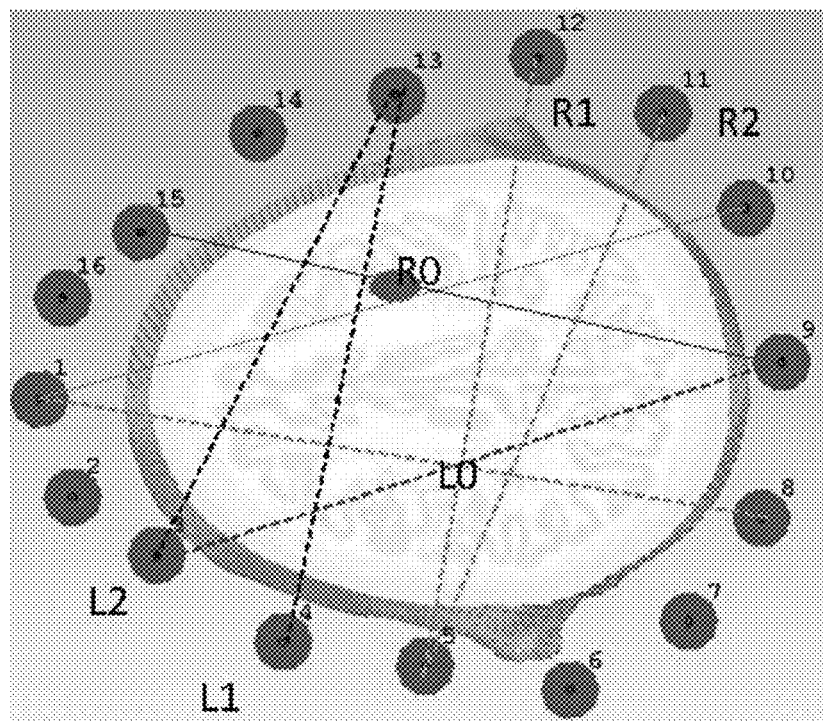
FIG. 21 is a schematic cross-sectional plan view of a subject's head surrounded by antennas, illustrating process steps for identifying which hemisphere of the subject's brain contains a feature of interest (such as a blood mass): two candidate intersection points (L0, R0) are in the left and right hemispheres, respectively; the 5$^{th}$ antenna to R1 across the L0 and R2 antenna is the adjacent antenna which is far away from L0 and R0; on the other hand, the 13$^{th}$ antenna to L1 nearly across the R0 apart from 5$^{th}$ antenna and L2 antenna is far away from L0 and R0.

FIG. 21 is a schematic cross-sectional plan view of a subject's head surrounded by antennas, illustrating the process steps (a) to (g). The differential weighted nodes between (5, R1, R2) are significantly different from the differential weighted nodes between (13, L1, L2), providing two potential candidates for the bleeding position (L0 or

R0). Following the steps above, it can be determined that the bleeding is located in the left hemisphere (at L0, not R0).

FIG. 19 is a flowchart of the localisation process. The output of the localisation process is a set containing antenna pairs and their respective assigned weights. Each weight corresponds to the probability of the signal passing through an abnormality such as a stroke, wherein a larger value indicates that the signal between the antenna pairs passes the stroke with high probability. Thus, the localisation process can determine those antenna pairs whose signals cross abnormalities, and this can be used to determine a real position for clinicians within a brain template.

By combining the signals with a brain template, the real position of a stroke can be computed using geometric methods. Given two independent pairs of antennas that contain an abnormality according to a high differential weighted node value, DW, the intersection between the pairs is determined to locate the stroke/abnormality. That is, the stroke location can be found as the intersection of the line between antenna pairs at positions (x1, y1) and (x2, y2) and the line between antenna pairs at positions (x3, y3) and (x4, y4). This intersection method can be extended to additional antenna pairs as shown in FIG. 19 for an example for 3 antenna pairs. The output of localization is the real position in the brain based on the brain template and the set of highly weighted antenna pairs.

Local-area Tomography 314

As a final verification, differential-equation tomography can be used for local area tomography at step 314, using the fused image 310 as an initial image. Specifically, the differential-equation tomography process described in International patent application No. PCT/AU2018/050425, entitled "A tomographic imaging system and process" is used to determine the exact dielectric properties of a suspected region identified by the beamography process 308 at different frequencies, and these determined properties are then used to determine the type of the abnormality. For example, higher dielectric properties (mainly permittivity) indicate a haemorrhage, whereas lower values indicate a clot. In the described process, the fused image is updated to include the more accurate dielectric properties of the suspected region determined by the differential-equation tomography process.

As described in the patent application, standard integral-based microwave tomography suffers from computational limitations, mainly due to the need for a Green's function. Those limitations prevent the image reconstruction process from being fast, which is an important requirement for urgent medical requirement in stroke detection. To cope with these limitations, significant approximations are usually utilized. Those approximations include considering the imaging antennas as point sources (which makes the problem underdetermined), assuming homogeneity along one of the domain's coordinate axes, and necessitating a background matching medium. These approximations result in the reconstruction of only two-dimensional images with certain level of error. To alleviate the aforementioned limitations and resultant challenges, the differential-equation based microwave tomography which is established on the wave and the third Maxwell equations, is utilized in this project. The proposed method is independent from the Green's function and its corresponding limitations. The method can rapidly reconstruct true three-dimensional images without any need to the above approximations, through solving a linear and determined problem.

If the resulting classification is different from that given by the classifier 312, the "Proof by Contradiction" method known to those skilled in the art is applied to obtain a reliable decision. As per this method, the tomography process is executed again, but this time starting with the classifier output. The convergence rate of the cost function in the second execution of the local-area tomography is compared with respect to the initial convergence rate that resulted in the first different answer. The convergence rate that reaches lower error degree is most probably the correct diagnosis. However, in the event that both methods converge to the same error level, another optimization method, such as Newton, Conjugate-Gradient or Contrast-Source is used.

In any case, the decision is verified using a Modified integral tomography process 316, as described below.

Global Tomography 316

Finally, at step 316 a global tomographic process based on modified integral-based tomography is applied to the initial bran template to verify the dielectric properties across the whole brain, including the suspected region.

Conventional integral-based tomography methods can be categorized into three types, depending upon whether they are based on the Born approximation, Newton iterative methods (distorted Born approximation), or contrast source inversion (CSI). Due to the desirable characteristics of high accuracy and low computational cost, CSI-based methods are attracting more interest for EM tomography. The traditional CSI method includes two optimization steps: the first step optimizes the contrast source, whereas the second step optimizes the contrast function based on the optimum contrast source from step 1. The optimum contrast function supplies the permittivity and conductivity information of the imaging area, which is the required final solution.

Based on numerous investigations of CSI-based methods, the inventors have found that the optimization of contrast source in step 1 is much easier than the optimization of contrast function in step 2. Accordingly, in the process described herein, only the contrast source is optimized using a conjugate gradient method. After the optimum contrast source is obtained, the brain template is used to calculate the total electric field using an FDTD/MOM forward solver. Since the contrast source is the product of the contrast function and the total electric field, the calculated electric field can be used to extract the contrast function from the optimized contrast source.

The formulations and procedures of this method can be summarized as follows:

1. Reconstruct the contrast source by using the conjugate gradient method.

$$w = \underset{w}{\mathrm{argmin}} \|G_\chi - S\|_2^2 \qquad (27)$$

where w is the contrast source, G is the Green function, and S is the received signal (S parameters).

2. Calculate the total electric field using the brain template and FDTD/MoM solver:

$$E_{tot} = f_{FDTD/MoM}(X_{temp}) \qquad (28)$$

where $E_{tot}$ is the electric field, $f_{FDTD/MoM}(\cdot)$ is the FDTD or MoM solver, and $X_{temp}$ is the brain template.

3. Extract the contrast function of the brain by using w and $E_{tot}$:

$$\chi = \frac{w}{E_{tot}} \qquad (29)$$

where x is the contrast function of the brain which contains the permittivity and conductivity information.

The described process provides three primary advantages:

1. Compared with the optimization of contrast function, the optimization of contrast source converges more rapidly and with greater accuracy;
2. The total electric field calculated using the brain template can generally be used to represent the electric field when abnormal tissues (e.g., a bleeding or clot) appears. Thus the optimization of the electric field under a stroke scenario is not necessary.
3. The extraction of the contrast function by using the contrast source and the electric field of the brain template is simple and stable.

The method described above uses a single frequency to reconstruct the electrical properties of the brain. However, due to the dispersive feature of bio-tissues, a multi-frequency method supplies more information with regard to electrical properties of the bio-tissues. Therefore, the inventors have also developed global tomography methods based on multiple frequencies. Specifically, four methods based on multi-frequencies have been developed, as described below.

1. Differential Sum-and-Mean Method (DSMM)

The first method is to sum the reconstructed conductivities under different frequencies and calculate the mean values. Assume the reconstructed differential contrast of each pixel under the frequency $f_n$ is denoted as $$\chi_{diff}^{f_n},$$

in which $$\chi_{diff}^{f_n}$$

is calculated as:

$$\chi_{diff} = \chi - \chi_{temp} \tag{30}$$

where $X_{temp}$ is the contrast of brain template, then the mean value of the reconstructed differential contrast under different frequencies is calculated as:

$$\chi_{diff}^{ave} = \frac{\sum_n^N \chi_{diff}^{f_n}}{N} \tag{31}$$

where N is the number of frequency samples.

2. Correlation Coefficient Method (CCM)

The described correlation coefficient method can be used to estimate the similarity of two set of signals. A value of correlation coefficient close to 1 indicates a high similarity between with the original signal, whereas a value close to 0 indicates dissimilarity. The method calculates a correlation coefficient map between the reconstructed conductivity distributions of the patient and the template. A region containing a stroke will present a high dissimilarity (low correlation coefficient) and regions without a stroke will present a high similarity (high correlation coefficient). The correlation coefficient for the reconstructed contrast distributions are calculated as:

$$\chi_{cc} = 1 - \frac{1}{N-1}\sum_n^N\left(\frac{\chi^{f_n}-\mu}{s}\right)\left(\frac{\chi_{temp}^{f_n}-\mu_{temp}}{s_{temp}}\right) \tag{32}$$

where s and $s_{temp}$ are the standard deviations of the reconstructed contrast under different frequencies for the patient and template, and $\mu$, $\mu_{temp}$ are the mean values of the reconstructed contrast under different frequencies.

3. Differential Entropy-Based Method (DEM)

Entropy is a measure of the uncertainty of a random variable. When the outcomes of an experiment are equiprobable (in other word, the probability distribution is uniform), the maximum value of entropy is obtained. Conversely, the minimum entropy value implies that a certain event has occurred. Therefore, the entropy value can also be used to measure the similarity between two set of signals. A low entropy value between the reconstructed contrast of a patient and the corresponding template head implies a stroke region, whereas a high entropy value implies a normal region. In the method used by the system described herein, the Rényi entropy is used with order 50. The Rényi entropy of the differential contrast is calculated as:

$$\chi_H = \frac{1}{1-\alpha}\log\left[\sum_n^N\left(\overline{\chi}_{diff}^{f_n}\right)^\alpha\right] \tag{33}$$

where $$\overline{\chi}_{diff}^{f_n}$$

is the normalized reconstructed contrast which is calculated as:

$$\overline{\chi}_{diff}^{f_n} = \frac{\chi_{diff}^{f_n}}{\sum_n^N \chi_{diff}^{f_n}} \tag{34}$$

4. Hybrid Method

Based on the results of using the DSMM, CCM and DEM described above, the inventors found that the different methods have their own merits and drawbacks. In particular, the DSMM is capable of localizing the position of stroke with desirable shape reconstruction, however, the artefact clusters are severe when compared with the results from CCM and DEM. The CCM is able to remove the artefact clusters; however, the position of stroke can shift, and consequently accurate localization cannot be achieved. Finally, the DEM can accurately localize the position of stroke while suppressing the artefact clusters; however, the shape of the stroke region suffers from distortions. In view of the above, the inventors have developed hybrid methods that combine these three methods so that the advantages of each method can be provided. The simplest of these hybrid method sums the results achieved from each of the methods to provide a hybrid image as according to:

$$\chi_{hybrid} = \frac{\chi_{diff}^{ave}}{\max(\chi_{diff}^{ave})} + \frac{\chi_{cc}}{\max(\chi_{cc})} + \frac{\chi_H}{\max(\chi_H)} \tag{35}$$

Image Fusion 310

Returning to the flow diagram of FIG. 3, to provide a single output image from the system to aid the diagnosis of brain stroke or trauma, at step 310 the image fusion process 310 generates a composite image of the subject's head. The fusion process combines complementary features of the head template, the beamography image, and the multi-frequency radar/tomography-based images, as shown in FIG. 20. The fusion enables the head boundary and high-resolution details of the head template to be combined with the target detection of beamography and the dielectric property estimation/refinement of tomography-based methods.

Several techniques can be used for image fusion. One method involves combining images based on wavelet or multi-scale features. In multi-scale transform based fusion, the high frequency components of one image (pertaining to useful image details such as 'edges') are extracted through a multi-scale transform, and then combined with another image (e.g., through substitution, addition, or a selection method) to generate a fused image. Other methods are based on training machine learning models to process features within the images and decide which are useful features to keep. This can be achieved through a model such as artificial neural networks (ANNs). Many other approaches exist for image fusion. Each fusion method has its own advantages that are favourable for the fusion process. For example, multi-scale transform based methods are suitable for multi-spectral images, and produce better frequency resolution outputs with more detailed features. ANNs are attractive for image fusion due to their ability to fuse images without going through complex computational effort. However, the use of a single technique might not be desirable due to limitations of resolution, or requirements for high quality training data, etc. Therefore, while using a single method produces promising outcomes, a method which combines the advantages of various techniques is desirable for more effective fusing.

In the system described herein, a hybrid process for image fusion is preferably used, involving several different fusion methods to process images, extracting important features and removing noise from different head imaging modalities (i.e. Beamography, Tomography). The results from different individual fusion techniques are then combined to build a fused image. The integration process combines the outcomes from the various methods and ensures that the final fused image inherits the merits of each fusion approach. It quantitatively and qualitatively enhances the quality of the fused image compared to the original images. Additionally, to further improve the accuracy of the fused image, a patient specific head template is also used in this fusion strategy. While inputs from Beamography and Tomography show the information of the inner tissues that are illuminated by electromagnetic signals, the head template provides information of the outer head layer based on the patient's actual 3D head surface. More importantly, the template also contains the relative distribution of brain tissues. Thus, it can be used in combination with features extracted from Beamography and Tomography to enhance the visual representation of inner brain tissue in the final fused image.

Many modifications will be apparent to those skilled in the art without departing from the scope of the present invention.

The invention claimed is:

1. A process for medical imaging, the process including:
(i) receiving scattering data representing mono-static or multi-static measurements of scattering of electromagnetic signals from tissues of a body part of a subject at a plurality of different signal frequencies, wherein the electromagnetic signals are emitted from one or more antennas and the corresponding scattered electromagnetic signals are measured by the one or more antennas;
(ii) using at least one processor, processing the scattering data to calculate electric field power values at each of a plurality of scattering locations of the subject's tissues within the body part and for each of the plurality of different signal frequencies;
(iii) using the at least one processor, for each of the plurality of scattering locations, summing the calculated electric field power values at the respective scattering location over the plurality of different signal frequencies and the one or more antennas to generate an image of the tissues within the body part; and
(iv) using the at least one processor, iteratively updating a model of the tissues within the body part based on a comparison of the model with the generated image until a termination criterion is satisfied, wherein the updated model is provided as an output image of the subject's tissues within the body part.

2. The process of claim 1, wherein the measurements are multi-static measurements and the one or more antennas comprise a plurality of antennas, wherein the electromagnetic signals are selectively emitted from each of the plurality of antennas disposed about the body part and the corresponding scattered electromagnetic signals are measured by each of the plurality of antennas.

3. The process of claim 1, wherein the body part is a head and the tissues include brain tissues of the subject.

4. The process of claim 1, including:
(v) processing biodata of the subject using machine learning to select, from a library of templates, a base template as being the best match for the subject, wherein the templates represent respective models of example tissues of the body part of respective subjects, and the biodata of the subject represents at least age, gender, weight, and ethnicity of the subject;
(vi) processing the selected base template and measurements of outer dimensions and/or shape of the subject's body part to generate template data representing the model of the tissues within the subject's body part by geometrically transforming spatial coordinates of the selected template to match the measurements of the subject's body part.

5. The process of claim 1, wherein the step of processing the scattering data includes the steps of:
(v) normalising and removing clutter from the scattering data; and
(vi) processing the normalised and clutter removed scattering data to calculate the electric field power values.

6. The process of claim 5, wherein removing clutter from the scattering data includes determining an average value of the measured scattered electromagnetic signals and subtracting the average value from each scattered electromagnetic signal measurement at each frequency to remove strong reflections and clutter from the scattering data.

7. The process of claim 1, including calibrating the scattering data by dividing measured scattering parameters for the body part by measured scattering parameters of an imaging domain in absence of the body part and with the imaging domain filled by a material with dielectric properties of a matching medium or an average body part phantom.

8. The process of claim 1, including classifying abnormal tissues within the body part as haemorrhagic or ischemic, by converting the scattering data from a frequency domain to a time-domain and mapping the time-domain scattering data to a corresponding graph, determining node degree and
degree sequence properties of the graph, calculating graph
degree mutual information to assess similarity of graphs,
and training a classifier with a training set of graph degree
mutual information features and their corresponding class
labels and applying the classifier to the graphs calculated for
the subject's tissues within the body part.

9. The process of claim 1, wherein the one or more
antennas comprise a plurality of antennas and the process
includes comparing the scattering data from corresponding
pairs of opposed antennas among the plurality of antennas to
identify significant differences between the scattering data
for different hemispheres of the subject's brain, these being
indicative of an abnormality in one of the hemispheres.

10. A non-transitory computer-readable storage medium
having stored thereon processor-executable instructions that,
when executed by the at least one processor of a medical
imaging system, cause the at least one processor to execute
the process of claim 1.

11. An apparatus for medical imaging, including:

(i) an input to receive scattering data representing mono-
static or multi-static measurements of scattering of
electromagnetic signals from tissues of a body part of
a subject at a plurality of different signal frequencies,
wherein the electromagnetic signals are emitted from
one or more antennas and the corresponding scattered
electromagnetic signals are measured by the one or
more antennas; and (ii) a processor configured to:

process the scattering data to calculate electric field
power values at each of a plurality of scattering
locations of the subject's tissues within the body part
and for each of the plurality of different signal
frequencies;

for each of the plurality of scattering locations, sum the
calculated electric field power values at the respec-
tive scattering location over the plurality of different
signal frequencies and the one or more antennas to
generate an image of the tissues within the body part;
and iteratively update a model of the tissues within the body
part based on a comparison of the model with the
generated image until a termination criterion is sat-
isfied, wherein the updated model is provided as an
output image of the subject's tissues within the body
part.

12. The apparatus of claim 11, wherein the measurements
are multi-static measurements and the one or more antennas
comprise a plurality of antennas, wherein the electromag-
netic signals are selectively emitted from each of the plu-
rality of antennas adapted to be disposed about the body part
and the corresponding scattered electromagnetic signals are
measured by each of the plurality of antennas.

13. The apparatus of claim 11, wherein the body part is a
head and the tissues include brain tissues of the subject.

14. The apparatus of claim 11, including a template
generator to:

process biodata of the subject using machine learning to
select, from a library of templates, a base template as
being the best match for the subject, wherein the
templates represent respective models of example tis-
sues of the body part of respective subjects, and the
biodata of the subject represents at least age, gender,
weight, and ethnicity of the subject; and process the selected base template and measurements of
outer dimensions and/or shape of the subject's body
part to generate template data representing the model of
the tissues within the subject's body part by geometri-
cally transforming spatial coordinates of the selected
template to match the measurements of the subject's
body part.

15. The apparatus of claim 11, wherein the processor is
configured to process the scattering data by:

(v) normalising and removing clutter from the scattering
data; and (vi) processing the normalised and clutter removed scat-
tering data to calculate the electric field power values.

16. The apparatus of claim 15, wherein the processor is
configured to remove clutter from the scattering data by
determining an average value of the measured scattered
electromagnetic signals and subtracting the average value
from each scattered electromagnetic signal measurement at
each frequency to remove strong reflections and clutter from
the scattering data.

17. The apparatus of claim 11, wherein the processor is
further configured to calibrate the scattering data by dividing
measured scattering parameters for the body part by mea-
sured scattering parameters of an imaging domain in
absence of the body part and with the imaging domain filled
by a material with dielectric properties of a matching
medium or an average body part phantom.

18. The apparatus of claim 11, wherein the processor is
further configured to classify abnormal tissues within the
body part as haemorrhagic or ischemic, by converting the
scattering data from a frequency domain to a time-domain
and mapping the time-domain scattering data to a corre-
sponding graph, to determine node degree and degree
sequence properties of the graph, to calculate graph degree
mutual information to assess similarity of graphs, and to
train a classifier with a training set of graph degree mutual
information features and their corresponding class labels and
apply the classifier to the graphs calculated for the subject's
tissues within the body part.

19. The apparatus of claim 11, wherein the one or more
antennas comprise a plurality of antennas and wherein the
processor is further configured to compare the scattering
data from corresponding pairs of opposed antennas among
the plurality of antennas to identify significant differences
between the scattering data for different hemispheres of the
subject's brain, these being indicative of an abnormality in
one of the hemispheres.

* * * * *